(12) United States Patent
Sato et al.

(10) Patent No.: US 10,517,482 B2
(45) Date of Patent: Dec. 31, 2019

(54) OPTICAL COHERENCE TOMOGRAPHY FOR ORTHODONTIC ALIGNERS

(71) Applicant: ALIGN TECHNOLOGY, INC., San Jose, CA (US)

(72) Inventors: Jun Sato, San Jose, CA (US); Allen Boronkay, San Jose, CA (US); Yaser Shanjani, Sunnyvale, CA (US); Reza Shirazi Aghjari, San Jose, CA (US); Avi Kopelman, Palo Alto, CA (US); Andrew Jang, San Mateo, CA (US); Jihua Cheng, San Jose, CA (US); Eric Kuo, San Jose, CA (US); Vladimir Shelbakh, Hayward, CA (US); Bastien Pesenti, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 16/048,054

(22) Filed: Jul. 27, 2018

(65) Prior Publication Data
US 2019/0029522 A1    Jan. 31, 2019

Related U.S. Application Data

(60) Provisional application No. 62/537,937, filed on Jul. 27, 2017.

(51) Int. Cl.
*G06T 7/73* (2017.01)
*A61B 5/00* (2006.01)
(Continued)

(52) U.S. Cl.
CPC .......... *A61B 5/0066* (2013.01); *A61B 5/0088* (2013.01); *A61B 5/4547* (2013.01);
(Continued)

(58) Field of Classification Search
None
See application file for complete search history.

(56) References Cited

U.S. PATENT DOCUMENTS

| 2,171,695 A | 9/1939 | Harper |
| 2,467,432 A | 4/1949 | Kesling |

(Continued)

FOREIGN PATENT DOCUMENTS

| AU | 517102 B | 11/1977 |
| AU | 3031677 A | 11/1977 |

(Continued)

OTHER PUBLICATIONS

US 8,553,966 B1, 10/2013, Alpern et al. (withdrawn)
(Continued)

*Primary Examiner* — Vu Nguyen
(74) *Attorney, Agent, or Firm* — Shay Glenn LLP

(57) ABSTRACT

Methods and apparatuses for 3D imaging (including 3D optical coherence tomography imaging) to measure the shape of orthodontic aligners, teeth, and other oral structures simultaneously, in-vivo or in-vitro. These methods and apparatuses may be used to determine contact locations of aligners with teeth and/or teeth with other teeth with very high precision, including determining the size of gaps where they are not in contact. These measurements may be used design, modify or replace an aligner and/or to verify aligner fit. 3D models of the whole aligner and teeth may be generated.

24 Claims, 21 Drawing Sheets

(51) Int. Cl.
  *A61C 7/00* (2006.01)
  *A61C 7/08* (2006.01)
  *A61C 7/10* (2006.01)
  *A61C 9/00* (2006.01)
  *A61C 13/00* (2006.01)
  *G06T 7/00* (2017.01)
  *G06T 15/08* (2011.01)

(52) U.S. Cl.
  CPC .......... *A61B 5/4848* (2013.01); *A61B 5/7257* (2013.01); *A61B 5/7425* (2013.01); *A61C 7/002* (2013.01); *A61C 7/08* (2013.01); *A61C 7/10* (2013.01); *A61C 9/0053* (2013.01); *A61C 13/0004* (2013.01); *G06T 7/0014* (2013.01); *G06T 7/75* (2017.01); *G06T 15/08* (2013.01); *A61B 2576/02* (2013.01); *G06T 2207/30036* (2013.01)

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,983,628 A | 10/1976 | Acevedo |
| 4,014,096 A | 3/1977 | Dellinger |
| 4,117,596 A | 10/1978 | Wallshein |
| 4,183,141 A | 1/1980 | Dellinger |
| 4,195,046 A | 3/1980 | Kesling |
| 4,253,828 A | 3/1981 | Coles et al. |
| 4,255,138 A | 3/1981 | Frohn |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,439,154 A | 3/1984 | Mayclin |
| 4,449,928 A | 5/1984 | von Weissenfluh |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A | 12/1986 | Lauks et al. |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,061,839 A | 10/1991 | Matsuno et al. |
| 5,083,919 A | 1/1992 | Quachi |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |

(56) References Cited

U.S. PATENT DOCUMENTS

| | | | |
|---|---|---|---|
| 5,542,842 | A | 8/1996 | Andreiko et al. |
| 5,543,780 | A | 8/1996 | McAuley et al. |
| 5,549,476 | A | 8/1996 | Stern |
| 5,562,448 | A | 10/1996 | Mushabac |
| 5,570,182 | A | 10/1996 | Nathel et al. |
| 5,583,977 | A | 12/1996 | Seidl |
| 5,587,912 | A | 12/1996 | Andersson et al. |
| 5,588,098 | A | 12/1996 | Chen et al. |
| 5,605,459 | A | 2/1997 | Kuroda et al. |
| 5,607,305 | A | 3/1997 | Andersson et al. |
| 5,614,075 | A | 3/1997 | Andre |
| 5,621,648 | A | 4/1997 | Crump |
| 5,626,537 | A | 5/1997 | Danyo et al. |
| 5,645,420 | A | 7/1997 | Bergersen |
| 5,645,421 | A | 7/1997 | Slootsky |
| 5,651,671 | A | 7/1997 | Seay et al. |
| 5,655,653 | A | 8/1997 | Chester |
| 5,659,420 | A | 8/1997 | Wakai et al. |
| 5,683,243 | A | 11/1997 | Andreiko et al. |
| 5,683,244 | A | 11/1997 | Truax |
| 5,691,539 | A | 11/1997 | Pfeiffer |
| 5,692,894 | A | 12/1997 | Schwartz et al. |
| 5,711,665 | A | 1/1998 | Adam et al. |
| 5,725,376 | A | 3/1998 | Poirier |
| 5,725,378 | A | 3/1998 | Wang |
| 5,730,151 | A | 3/1998 | Summer et al. |
| 5,737,084 | A | 4/1998 | Ishihara |
| 5,740,267 | A | 4/1998 | Echerer et al. |
| 5,742,700 | A | 4/1998 | Yoon et al. |
| 5,769,631 | A | 6/1998 | Williams |
| 5,774,425 | A | 6/1998 | Ivanov et al. |
| 5,790,242 | A | 8/1998 | Stern et al. |
| 5,799,100 | A | 8/1998 | Clarke et al. |
| 5,800,174 | A | 9/1998 | Andersson |
| 5,813,854 | A | 9/1998 | Nikodem |
| 5,816,800 | A | 10/1998 | Brehm et al. |
| 5,818,587 | A | 10/1998 | Devaraj et al. |
| 5,823,778 | A | 10/1998 | Schmitt et al. |
| 5,848,115 | A | 12/1998 | Little et al. |
| 5,857,853 | A | 1/1999 | van Nifterick et al. |
| 5,866,058 | A | 2/1999 | Batchelder et al. |
| 5,879,158 | A | 3/1999 | Doyle et al. |
| 5,880,961 | A | 3/1999 | Crump |
| 5,880,962 | A | 3/1999 | Andersson et al. |
| 5,886,702 | A | 3/1999 | Migdal et al. |
| 5,890,896 | A | 4/1999 | Padial |
| 5,904,479 | A | 5/1999 | Staples |
| 5,934,288 | A | 8/1999 | Avila et al. |
| 5,957,686 | A | 9/1999 | Anthony |
| 5,964,587 | A | 10/1999 | Sato |
| 5,971,754 | A | 10/1999 | Sondhi et al. |
| 5,975,893 | A | 11/1999 | Chishti et al. |
| 5,975,906 | A | 11/1999 | Knutson |
| 5,980,246 | A | 11/1999 | Ramsay et al. |
| 5,989,023 | A | 11/1999 | Summer et al. |
| 6,002,706 | A | 12/1999 | Stayer et al. |
| 6,044,309 | A | 3/2000 | Honda |
| 6,049,743 | A | 4/2000 | Baba |
| 6,053,731 | A | 4/2000 | Heckenberger |
| 6,068,482 | A | 5/2000 | Snow |
| 6,070,140 | A | 5/2000 | Tran |
| 6,099,303 | A | 8/2000 | Gibbs et al. |
| 6,099,314 | A | 8/2000 | Kopelman et al. |
| 6,123,544 | A | 9/2000 | Cleary |
| 6,152,731 | A | 11/2000 | Jordan et al. |
| 6,154,676 | A | 11/2000 | Levine |
| 6,183,248 | B1 | 2/2001 | Chishti et al. |
| 6,183,249 | B1 | 2/2001 | Brennan et al. |
| 6,186,780 | B1 | 2/2001 | Hibst et al. |
| 6,190,165 | B1 | 2/2001 | Andreiko et al. |
| 6,200,133 | B1 | 3/2001 | Kittelsen |
| 6,201,880 | B1 | 3/2001 | Elbaum et al. |
| 6,212,435 | B1 | 4/2001 | Lattner et al. |
| 6,217,334 | B1 | 4/2001 | Hultgren |
| 6,227,850 | B1 | 5/2001 | Chishti et al. |
| 6,231,338 | B1 | 5/2001 | de Josselin de Jong et al. |
| 6,239,705 | B1 | 5/2001 | Glen |
| 6,243,601 | B1 | 6/2001 | Wist |
| 6,263,234 | B1 | 7/2001 | Engelhardt et al. |
| 6,283,761 | B1 | 9/2001 | Joao |
| 6,299,438 | B1 | 10/2001 | Sahagian et al. |
| 6,309,215 | B1 | 10/2001 | Phan et al. |
| 6,313,432 | B1 | 11/2001 | Nagata et al. |
| 6,315,553 | B1 | 11/2001 | Sachdeva et al. |
| 6,328,745 | B1 | 12/2001 | Ascherman |
| 6,334,073 | B1 | 12/2001 | Levine |
| 6,350,120 | B1 | 2/2002 | Sachdeva et al. |
| 6,364,660 | B1 | 4/2002 | Durbin et al. |
| 6,382,975 | B1 | 5/2002 | Poirier |
| 6,386,878 | B1 | 5/2002 | Pavlovskaia et al. |
| 6,402,510 | B1 | 6/2002 | Williams |
| 6,402,707 | B1 | 6/2002 | Ernst |
| 6,405,729 | B1 | 6/2002 | Thornton |
| 6,406,292 | B1 | 6/2002 | Chishti et al. |
| 6,409,504 | B1 | 6/2002 | Jones et al. |
| 6,413,086 | B1 | 7/2002 | Womack |
| 6,414,264 | B1 | 7/2002 | von Falkenhausen |
| 6,414,708 | B1 | 7/2002 | Carmeli et al. |
| 6,436,058 | B1 | 8/2002 | Krahner et al. |
| 6,450,167 | B1 | 9/2002 | David et al. |
| 6,450,807 | B1 | 9/2002 | Chishti et al. |
| 6,462,301 | B1 | 10/2002 | Scott et al. |
| 6,471,511 | B1 | 10/2002 | Chishti et al. |
| 6,471,512 | B1 | 10/2002 | Sachdeva et al. |
| 6,471,970 | B1 | 10/2002 | Fanara et al. |
| 6,482,002 | B2 | 11/2002 | Jordan et al. |
| 6,482,298 | B1 | 11/2002 | Bhatnagar |
| 6,496,814 | B1 | 12/2002 | Busche |
| 6,496,816 | B1 | 12/2002 | Thiesson et al. |
| 6,499,026 | B1 | 12/2002 | Rivette et al. |
| 6,499,995 | B1 | 12/2002 | Schwartz |
| 6,507,832 | B1 | 1/2003 | Evans et al. |
| 6,514,074 | B1 | 2/2003 | Chishti et al. |
| 6,515,593 | B1 | 2/2003 | Stark et al. |
| 6,516,288 | B2 | 2/2003 | Bagne |
| 6,516,805 | B1 | 2/2003 | Thornton |
| 6,520,772 | B2 | 2/2003 | Williams |
| 6,523,019 | B1 | 2/2003 | Borthwick |
| 6,524,101 | B1 | 2/2003 | Phan et al. |
| 6,526,168 | B1 | 2/2003 | Ornes et al. |
| 6,529,891 | B1 | 3/2003 | Heckerman |
| 6,529,902 | B1 | 3/2003 | Kanevsky et al. |
| 6,532,455 | B1 | 3/2003 | Martin et al. |
| 6,535,865 | B1 | 3/2003 | Skaaning et al. |
| 6,540,512 | B1 | 4/2003 | Sachdeva et al. |
| 6,540,707 | B1 | 4/2003 | Stark et al. |
| 6,542,593 | B1 | 4/2003 | Bowman Amuah |
| 6,542,881 | B1 | 4/2003 | Meidan et al. |
| 6,542,894 | B1 | 4/2003 | Lee et al. |
| 6,542,903 | B2 | 4/2003 | Hull et al. |
| 6,551,243 | B2 | 4/2003 | Bocionek et al. |
| 6,556,659 | B1 | 4/2003 | Bowman Amuah |
| 6,556,977 | B1 | 4/2003 | Lapointe et al. |
| 6,560,592 | B1 | 5/2003 | Reid et al. |
| 6,564,209 | B1 | 5/2003 | Dempski et al. |
| 6,567,814 | B1 | 5/2003 | Bankier et al. |
| 6,571,227 | B1 | 5/2003 | Agrafiotis et al. |
| 6,572,372 | B1 | 6/2003 | Phan et al. |
| 6,573,998 | B2 | 6/2003 | Cohen Sabban |
| 6,574,561 | B2 | 6/2003 | Alexander et al. |
| 6,578,003 | B1 | 6/2003 | Camarda et al. |
| 6,580,948 | B2 | 6/2003 | Haupert et al. |
| 6,587,529 | B1 | 7/2003 | Staszewski et al. |
| 6,587,828 | B1 | 7/2003 | Sachdeva |
| 6,594,539 | B1 | 7/2003 | Geng |
| 6,595,342 | B1 | 7/2003 | Maritzen et al. |
| 6,597,934 | B1 | 7/2003 | de Jong et al. |
| 6,598,043 | B1 | 7/2003 | Baclawski |
| 6,599,250 | B2 | 7/2003 | Webb et al. |
| 6,602,070 | B2 | 8/2003 | Miller et al. |
| 6,604,527 | B1 | 8/2003 | Palmisano |
| 6,606,744 | B1 | 8/2003 | Mikurak |
| 6,607,382 | B1 | 8/2003 | Kuo et al. |
| 6,611,783 | B2 | 8/2003 | Kelly et al. |

(56) References Cited

U.S. PATENT DOCUMENTS

| | | |
|---|---|---|
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,790,036 B2 | 9/2004 | Graham |
| 6,830,450 B2 | 12/2004 | Knopp et al. |
| 6,832,912 B2 | 12/2004 | Mao |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,984,128 B2 | 1/2006 | Breining et al. |
| 7,036,514 B2 | 5/2006 | Heck |
| 7,040,896 B2 | 5/2006 | Paylovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,192,273 B2 | 3/2007 | McSurdy |
| 7,220,122 B2 | 5/2007 | Chishti |
| 7,220,124 B2 | 5/2007 | Taub et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy |
| 7,874,849 B2 | 1/2011 | Sticker et al. |
| 7,878,801 B2 | 2/2011 | Abolfathi et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,077,949 B2 | 12/2011 | Liang et al. |
| 8,083,556 B2 | 12/2011 | Stadler et al. |
| D652,799 S | 1/2012 | Mueller |
| 8,099,305 B2 | 1/2012 | Kuo et al. |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,172,569 B2 | 5/2012 | Matty et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |

(56) References Cited

U.S. PATENT DOCUMENTS

| | | |
|---|---|---|
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,433,083 B2 | 4/2013 | Abolfathi et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rösch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,214,014 B2 | 12/2015 | Levin |
| 9,241,774 B2 | 1/2016 | Li et al. |
| 9,242,118 B2 | 1/2016 | Brawn |
| 9,261,358 B2 | 2/2016 | Atiya et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,584,771 B2 | 2/2017 | Mandelis et al. |
| 9,589,329 B2 | 3/2017 | Levin |
| 9,675,430 B2 | 6/2017 | Verker et al. |
| 9,693,839 B2 | 7/2017 | Atiya et al. |
| 9,744,006 B2 | 8/2017 | Ross |
| 9,830,688 B2 | 11/2017 | Levin |
| 9,861,451 B1 | 1/2018 | Davis |
| 9,936,186 B2 | 4/2018 | Jesenko et al. |
| 10,159,541 B2 | 12/2018 | Bindayel |
| 10,195,690 B2 | 2/2019 | Culp |
| 10,231,801 B2 | 3/2019 | Korytov et al. |
| 10,238,472 B2 | 3/2019 | Levin |
| 10,258,432 B2 | 4/2019 | Webber |
| 2001/0002310 A1 | 5/2001 | Chishti et al. |
| 2001/0038705 A1 | 11/2001 | Rubbert et al. |
| 2001/0041320 A1 | 11/2001 | Phan et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0064752 A1 | 5/2002 | Durbin et al. |
| 2002/0064759 A1 | 5/2002 | Durbin et al. |
| 2002/0107853 A1 | 8/2002 | Hofmann et al. |
| 2002/0188478 A1 | 12/2002 | Breeland et al. |
| 2003/0000927 A1 | 1/2003 | Kanaya et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0068598 A1 | 4/2003 | Vallittu et al. |
| 2003/0095697 A1 | 5/2003 | Wood et al. |
| 2003/0139834 A1 | 7/2003 | Nikolskiy et al. |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0215764 A1 | 11/2003 | Kopelman et al. |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0094165 A1 | 5/2004 | Cook |
| 2004/0133083 A1 | 7/2004 | Comaniciu et al. |
| 2004/0158194 A1 | 8/2004 | Wolff et al. |
| 2004/0167646 A1 | 8/2004 | Jelonek et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0220691 A1 | 11/2004 | Hofmeister et al. |
| 2004/0259049 A1 | 12/2004 | Kopelman et al. |
| 2005/0003318 A1 | 1/2005 | Choi et al. |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0048433 A1 | 3/2005 | Hilliard |
| 2005/0074717 A1 | 4/2005 | Cleary et al. |
| 2005/0100333 A1 | 5/2005 | Kerschbaumer et al. |
| 2005/0108052 A1 | 5/2005 | Omaboe |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0098007 A1 | 5/2006 | Rouet et al. |
| 2006/0099546 A1 | 5/2006 | Bergersen |
| 2006/0111631 A1 | 5/2006 | Kelliher et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |

(56) References Cited

U.S. PATENT DOCUMENTS

| | | |
|---|---|---|
| 2006/0188834 A1 | 8/2006 | Hilliard |
| 2006/0199153 A1 | 9/2006 | Liu et al. |
| 2006/0223022 A1 | 10/2006 | Solomon |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275736 A1 | 12/2006 | Wen et al. |
| 2006/0290693 A1 | 12/2006 | Zhou et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0087300 A1 | 4/2007 | Willison et al. |
| 2007/0106138 A1 | 5/2007 | Beiski et al. |
| 2007/0141526 A1 | 6/2007 | Eisenberg et al. |
| 2007/0168152 A1 | 7/2007 | Matov et al. |
| 2007/0172112 A1 | 7/2007 | Paley et al. |
| 2007/0184402 A1 | 8/2007 | Boutoussov et al. |
| 2007/0199929 A1 | 8/2007 | Rippl et al. |
| 2007/0215582 A1 | 9/2007 | Roeper et al. |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057479 A1 | 3/2008 | Grenness |
| 2008/0090208 A1 | 4/2008 | Rubbert |
| 2008/0094389 A1 | 4/2008 | Rouet et al. |
| 2008/0115791 A1 | 5/2008 | Heine |
| 2008/0118886 A1* | 5/2008 | Liang .................. A61B 5/0088 433/29 |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0268400 A1 | 10/2008 | Moss et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0181346 A1 | 7/2009 | Orth |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0317757 A1 | 12/2009 | Lemchen |
| 2010/0019170 A1 | 1/2010 | Hart et al. |
| 2010/0045902 A1 | 2/2010 | Ikeda et al. |
| 2010/0068676 A1 | 3/2010 | Mason et al. |
| 2010/0086890 A1 | 4/2010 | Kuo |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0193482 A1 | 8/2010 | Ow et al. |
| 2010/0216085 A1 | 8/2010 | Kopelman |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0143300 A1 | 6/2011 | Villaalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0029883 A1 | 2/2012 | Heinz et al. |
| 2012/0040311 A1 | 2/2012 | Nilsson |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0122027 A1 | 5/2014 | Andreiko et al. |
| 2014/0142902 A1 | 5/2014 | Chelnokov et al. |
| 2014/0265034 A1 | 9/2014 | Dudley |
| 2014/0272774 A1 | 9/2014 | Dillon et al. |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0350354 A1 | 11/2014 | Stenzler et al. |
| 2014/0363778 A1 | 12/2014 | Parker |
| 2015/0002649 A1 | 1/2015 | Nowak et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0150501 A1 | 6/2015 | George et al. |
| 2015/0164335 A1 | 6/2015 | Van Der Poel et al. |

(56) References Cited

U.S. PATENT DOCUMENTS

| | | |
|---|---|---|
| 2015/0173856 A1 | 6/2015 | Iowe et al. |
| 2015/0216626 A1 | 8/2015 | Ranjbar |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220200 A1* | 8/2016 | Sandholm ............... A61B 8/08 |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049311 A1 | 2/2017 | Borovinskih et al. |
| 2017/0049326 A1 | 2/2017 | Alfano et al. |
| 2017/0056131 A1 | 3/2017 | Alauddin et al. |
| 2017/0071705 A1 | 3/2017 | Kuo |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0251954 A1 | 9/2017 | Lotan et al. |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1 | 3/2018 | Ha |
| 2018/0085059 A1 | 3/2018 | Lee |
| 2018/0096465 A1 | 4/2018 | Levin |
| 2018/0125610 A1 | 5/2018 | Carrier et al. |
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2019/0046297 A1 | 2/2019 | Kopelman et al. |
| 2019/0076216 A1 | 3/2019 | Moss et al. |
| 2019/0090983 A1 | 3/2019 | Webber et al. |

FOREIGN PATENT DOCUMENTS

| | | |
|---|---|---|
| AU | 5598894 A | 6/1994 |
| CA | 1121955 A1 | 4/1982 |
| CN | 102017658 A | 4/2011 |
| CN | 105496575 A | 4/2016 |
| CN | 105997274 A | 10/2016 |
| DE | 2749802 A1 | 5/1978 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 09-19443 A | 1/1997 |
| JP | 2000339468 A | 9/2004 |
| JP | 2006043121 A | 2/2006 |
| JP | 2007260158 A | 10/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20090065778 A | 6/2009 |
| KR | 10-1266966 B1 | 5/2013 |
| KR | 10-2016-041632 A | 4/2016 |
| KR | 10-2016-0071127 A | 6/2016 |
| KR | 10-1675089 B1 | 11/2016 |
| WO | WO91/004713 A1 | 4/1991 |
| WO | WO94/010935 A1 | 5/1994 |
| WO | WO98/032394 A1 | 7/1998 |
| WO | WO98/044865 A1 | 10/1998 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/100700 A1 | 9/2006 |
| WO | WO2006/133548 A1 | 12/2006 |
| WO | WO2007/071341 A1 | 6/2007 |
| WO | WO2008/115654 A1 | 9/2008 |
| WO | WO2009/016645 A2 | 2/2009 |

(56) References Cited

FOREIGN PATENT DOCUMENTS

| | | |
|---|---|---|
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |
| WO | WO2018/232113 A1 | 12/2018 |
| WO | WO2019/018784 A1 | 1/2019 |

OTHER PUBLICATIONS

AADR. American Association for Dental Research; Summary of Activities; Los Angeles, CA; p. 195; Mar. 20-23,(year of pub. sufficiently earlier than effective US filing date and any foreign priority date) 1980.
Alcaniz et aL; An Advanced System for the Simulation and Planning of Orthodontic Treatments; Karl Heinz Hohne and Ron Kikinis (eds.); Visualization in Biomedical Computing, 4th Intl. Conf. VBC '96, Hamburg, Germany; Springer-Verlag; pp. 511-520; Sep. 22-25, 1996.
Alexander et al.; The DigiGraph Work Station Part 2 Clinical Management; J. Clin. Orthod.; pp. 402-407; (Author Manuscript); Jul. 1990.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.
Allesee Orthodontic Appliances: DuraClearTM; Product information; 1 page; (year of pub. sufficiently earlier than effective US filing date and any foreign priority date) 1997.
Allesee Orthodontic Appliances; The Choice is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.
Allesee Orthodontic Appliances; The Choice is Clear: Red, White & Blue . . . The Simple, Affordable, No-Braces Treatment; (product information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Begole et al.; A Computer System for the Analysis of Dental Casts; The Angle Orthodontist; 51(3); pp. 252-258; Jul. 1981.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biggerstaff; Computerized Diagnostic Setups and Simulations; Angle Orthodontist; 40(I); pp. 28-36; Jan. 1970.
Biostar Operation & Training Manual. Great Lakes Orthodontics, Ltd. 199 Fire Tower Drive,Tonawanda, New York. 14150-5890, 20

(56) References Cited

OTHER PUBLICATIONS pages; (year of pub. sufficiently earlier than effective US filing date and any foreign priority date) 1990.

Blu et al.; Linear interpolation revitalized; IEEE Transactions on Image Processing; 13(5); pp. 710-719; May 2004.

Bourke, Coordinate System Transformation; 1 page; retrived from the internet (http://astronomy.swin.edu.au/' pbourke/prolection/coords) on Nov. 5, 2004; Jun. 1996.

Boyd et al.; Three Dimensional Diagnosis and Orthodontic Treatment of Complex Malocclusions With the Invisalipn Appliance; Seminars in Orthodontics; 7(4); pp. 274-293; Dec. 2001.

Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.

Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.

Burstone et al.; Precision Adjustment of the Transpalatal Lingual Arch: Computer Arch Form Predetermination; American Journal of Orthodontics; 79(2);pp. 115-133; Feb. 1981.

Burstone; Dr. Charles J. Burstone on The Uses of the Computer in Orthodontic Practice (Part 1); Journal of Clinical Orthodontics; 13(7); pp. 442-453; (interview); Jul. 1979.

Burstone; Dr. Charles J. Burstone on The Uses of the Computer in Orthodontic Practice (Part 2); journal of Clinical Orthodontics; 13(8); pp. 539-551 (interview); Aug. 1979.

Cardinal Industrial Finishes; Powder Coatings; 6 pages; retrieved from the internet (http://www.cardinalpaint.com) on Aug. 25, 2000.

Carnaghan, An Alternative to Holograms for the Portrayal of Human Teeth; 4th Int'l. Conf. on Holographic Systems, Components and Applications; pp. 228-231; Sep. 15, 1993.

Chaconas et al.,; The DigiGraph Work Station, Part 1, Basic Concepts; Journal of Clinical Orthodontics; 24(6); pp. 360-367; (Author Manuscript); Jun. 1990.

Chafetz et al.; Subsidence of the Femoral Prosthesis, A Stereophotogrammetric Evaluation; Clinical Orthopaedics and Related Research; No. 201; pp. 60-67; Dec. 1985.

Chiappone; Constructing the Gnathologic Setup and Positioner; Journal of Clinical Orthodontics; 14(2); pp. 121-133; Feb. 1980.

Chishti et al.; U.S. Appl. No. 60/050,342 entitled "Procedure for moving teeth using a seires of retainers," filed Jun. 20, 1997.

CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.

Cottingham; Gnathologic Clear Plastic Positioner; American Journal of Orthodontics; 55(1); pp. 23-31; Jan. 1969.

Crawford; CAD/CAM in the Dental Office: Does It Work?; Canadian Dental Journal; 57(2); pp. 121-123 Feb. 1991.

Crawford; Computers in Dentistry: Part 1: CAD/CAM: The Computer Moves Chairside, Part 2: F. Duret A Man With A Vision, Part 3: The Computer Gives New Vision—Literally, Part 4: Bytes 'N Bites The Computer Moves From the Front Desk to The Operatory; Canadian Dental Journal; 54(9); pp. 661-666 Sep. 1988.

Crooks; CAD/CAM Comes to USC; USC Dentistry; pp. 14-17; (year of pub. sufficiently earlier than effective US filing date and any foreign priority date) Spring 1990.

Cureton; Correcting Malaligned Mandibular Incisors with Removable Retainers; Journal of Clinical Orthodontics; 30(7); pp. 390-395; Jul. 1996.

Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.

Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.

DCS Dental AG; The CAD/CAM 'DCS Titan System' for Production of Crowns/Bridges; DSC Production; pp. 1-7; Jan. 1992.

Defranco et al.; Three-Dimensional Large Displacement Analysis of Orthodontic Appliances; Journal of Biomechanics; 9(12); pp. 793-801; Jan. 1976.

Dental Institute University of Zurich Switzerland; Program for International Symposium on Computer Restorations: State of the Art of the CEREC-Method; 2 pages; May 1991.

Dentrac Corporation; Dentrac document; pp. 4-13; (year of pub. sufficiently earlier than effective US filing date and any foreign priority date) 1992.

Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.

Di Muzio et al.; Minimum intensity projection (MinIP); 6 pages; retrieved from the internet (https://radiopaedia.org/articles/minimum-intensity-projection-minip) on Sep. 6, 2018.

Doruk et al.; The role of the headgear timer in extraoral co-operation; European Journal of Orthodontics; 26; pp. 289-291; Jun. 1, 2004.

Doyle; Digital Dentistry; Computer Graphics World; pp. 50-52 andp. 54; Oct. 2000.

Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.

Duret et al.; CAD/CAM Imaging in Dentistry; Current Opinion in Dentistry; 1(2); pp. 150-154; Apr. 1991.

Duret et al; CAD-CAM in Dentistry; Journal of the American Dental Association; 117(6); pp. 715-720; Nov. 1988.

Duret; The Dental CAD/CAM, General Description of the Project; Hennson International Product Brochure, 18 pages; Jan. 1986.

Duret; Vers Une Prosthese Informatisee; Tonus; 75(15); pp. 55-57; (English translation attached); 23 pages; Nov. 15, 1985.

Economides; The Microcomputer in the Orthodontic Office; Journal of Clinical Orthodontics; 13(11); pp. 767-772; Nov. 1979.

Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.

Elsasser; Some Observations on the History and Uses of the Kesling Positioner; American Journal of Orthodontics; 36(5); pp. 368-374; May 1, 1950.

English translation of Japanese Laid-Open Publication No. 63-11148 to inventor T. Ozukuri (Laid-Open on Jan. 18, 1998) pp. 1-7.

Faber et al.; Computerized Interactive Orthodontic Treatment Planning; American Journal of Orthodontics; 73(1); pp. 36-46; Jan. 1978.

Felton et al.; A Computerized Analysis of the Shape and Stability of Mandibular Arch Form; American Journal of Orthodontics and Dentofacial Orthopedics; 92(6); pp. 478-483; Dec. 1987.

Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.

Friede et al.; Accuracy of Cephalometric Prediction in Orthognathic Surgery; Journal of Oral and Maxillofacial Surgery; 45(9); pp. 754-760; Sep. 1987.

Friedrich et al; Measuring system for in vivo recording of force systems in orthodontic treatment-concept and analysis of accuracy; J. Biomech.; 32(1); pp. 81-85; (Abstract Only) Jan. 1999.

Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

(56) References Cited

OTHER PUBLICATIONS

Gim-Alldent Deutschland, "Das DUX System: Die Technik," 3 pages; (English Translation Included); (year of pub. sufficiently earlier than effective US filing date and any foreign priority date); 2002.

Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Grest, Daniel; Marker-Free Human Motion Capture in Dynamic Cluttered Environments from a Single View-Point, PhD Thesis; 171 pages; Dec. 2007.

Guess et al.; Computer Treatment Estimates in Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . . ); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

Invisalign; You were made to move. There's never been a better time to straighten your teeth with the most advanced clear aligner in the world; Product webpage; 2 pages; retrieved from the internet (www.invisalign.com/) on Dec. 28, 2017.

JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kumar et al.; Rapid maxillary expansion: A unique treatment modality in dentistry; J. Clin. Diagn. Res.; 5(4); pp. 906-911; Aug. 2011.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

McCann; Inside the ADA; J. Amer. Dent. Assoc, 118:286-294; Mar. 1989.

McNamara et al.; Invisible Retainers; J. Clin Orthod.; pp. 570-578; 11 pages; (Author Manuscript); Aug. 1985.

McNamara et al.; Orthodontic and Orthopedic Treatment in the Mixed Dentition; Needham Press; pp. 347-353; Jan. 1993.

Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.

Moles; Correcting Mild Malalignments—As Easy As One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; CEREC CAD/CAM Inlays: Aesthetics and Durability in a Single Appointment; Dentistry Today; 9(8); pp. 20, 22-23 and 54; Oct. 1990.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Ogawa et al.; Mapping, profiling and clustering of pressure pain threshold (PPT) in edentulous oral muscosa; Journal of Dentistry; 32(3); pp. 219-228; Mar. 2004.

Ogimoto et al.; Pressure-pain threshold determination in the oral mucosa; Journal of Oral Rehabilitation; 29(7); pp. 620-626; Jul. 2002.

Paul et al.; Digital Documentation of Individual Human Jaw and Tooth Forms for Applications in Orthodontics; Oral Surgery and

(56) References Cited

OTHER PUBLICATIONS

Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages, Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.

Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date).
Sturman; Interactive Keyframe Animation of 3-D Articulated Models; Proceedings Graphics Interface '84; vol. 86; pp. 35-40; May-Jun. 1984.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thera Mon; "Microsensor"; 2 pages; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-8; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.

(56) References Cited

OTHER PUBLICATIONS

Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models'An Introduction; Computer-Aided Design; 29(4); pp. 255-268; 20 pages; (Author Manuscript); Apr. 1997.
Verstreken et al.; An Image-Guided Planning System for Endosseous Oral Implants; IEEE Transactions on Medical Imaging; 17(5); pp. 842-852; Oct. 1998.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Watson et al.; Pressures recorded at te denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Wikipedia; Palatal expansion; 3 pages; retrieved from the internet (https://en.wikipedia.org/wiki/Palatal_expansion) on Mar. 5, 2018.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Witt et al.; The wear-timing measuring device in orthodontics-cui Bono? Reflections on the state-of-the-art in wear-timing measurement and compliance research in orthodontics; Fortschr Kieferorthop.; 52(3); pp. 117-125; (Translation Included) Jun. 1991.
Wolf; Three-dimensional structure determination of semitransparent objects from holographic data; Optics Communications; 1(4); pp. 153-156; Sep. 1969.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamada et al.; Simulation of fan-beam type optical computed-tomography imaging of strongly scattering and weakly absorbing media; Applied Optics; 32(25); pp. 4808-4814; Sep. 1, 1993.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Grove et al.; U.S. Appl. No. 15/726,243 entitled "Interproximal reduction templates," filed Oct. 5, 2017.
Cramer; U.S. Appl. No. 15/937,569 entitled "Apparatuses and methods assisting in dental therapies," filed Mar. 27, 2018.
Cramer et al.; U.S. Appl. No. 15/942,341 entitled "Orthodontic appliances including at least partially un-erupted teeth and method of forming them," filed Mar. 30, 2018.
Shanjani et al.; U.S. Appl. No. 16/019,037 entitled "Biosensor performance indicator for intraoral appliances," filed Jun. 26, 2018.
Riley et al.; U.S. Appl. No. 16/003,841 entitled Palatal expander with skeletal anchorage devices, filed Jun. 8, 2018.
Sato et al.; U.S. Appl. No. 16/041,606 entitled "Palatal contour anchorage," filed Jul. 20, 2018.
Xue et al.; U.S. Appl. No. 16/010,087 entitled "Automatic detection of tooth type and eruption status," filed Jun. 15, 2018.
Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.
Arakawa et al; Mouthguard biosensor with telemetry system for monitoring of saliva glucose: A novel cavitas sensor; Biosensors and Bioelectronics; 84; pp. 106-111; Oct. 2016.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." Dec. 24, 2018.
Kopleman et al., U.S. Appl. No. 16/220,381 entitled "Closed loop adaptive orthodontic treatment methods and apparatuses," Dec. 14, 2018.
Farooq et al.; Relationship between tooth dimensions and malocclusion; JPMA: The Journal of the Pakistan Medical Association; 64(6); pp. 670-674; Jun. 2014.
Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
Ormco.com; Increasing clinical performance with 3D interactive treatment planning and patient-specific appliances; 8 pages; retrieved from the internet (http://www.konsident.com/wp-content/files_mf/1295385693http_ormco.com_index_cmsfilesystemaction_fileOrmcoPDF_whitepapers.pdf) on Feb. 27, 2019.
Video of DICOM to Surgical Guides; Can be viewed at <URL:https://youtu.be/47KtOmCEFQk; Published Apr. 4, 2016.
Sabina et al., U.S. Appl. No. 16/258,516 entitled "Diagnostic intraoral scanning" filed Jan. 25, 2019.
Sabina et al., U.S. Appl. No. 16/258,523 entitled "Diagnostic intraoral tracking" filed Jan. 25, 2019.
Sabina et al., U.S. Appl. No. 16/258,527 entitled "Diagnostic intraoral methods and apparatuses" filed Jan. 25, 2019.
Li et al.; U.S. Appl. No. 16/171,159 entitled "Alternative bite adjustment structures," filed Oct. 25, 2018.
Culp; U.S. Appl. No. 16/236,220 entitled "Laser cutting," filed Dec. 28, 2018.

(56) References Cited

OTHER PUBLICATIONS

Culp; U.S. Appl. No. 16/265,287 entitled "Laser cutting," filed Feb. 1, 2019.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Bandodkar et al.; All-printed magnetically self-healing electrochemical devices; Science Advances; 2(11); 11 pages; e1601465; Nov. 2016.
Bandodkar et al.; Self-healing inks for autonomous repair of printable electrochemical devices; Advanced Electronic Materials; 1(12); 5 pages; 1500289; Dec. 2015.
Bandodkar et al.; Wearable biofuel cells: a review; Electroanalysis; 28(6); pp. 1188-1200; Jun. 2016.
Bandodkar et al.; Wearable chemical sensors: present challenges and future prospects; Acs Sensors; 1(5); pp. 464-482; May 11, 2016.
Imani et al.; A wearable chemical-electrophysiological hybrid biosensing system for real-time health and fitness monitoring; Nature Communications; 7; 11650. doi 1038/ncomms11650; 7 pages; May 23, 2016.
Jia et al.; Epidermal biofuel cells: energy harvesting from human perspiration; Angewandle Chemie International Edition; 52(28); pp. 7233-7236; Jul. 8, 2013.
Jia et al.; Wearable textile biofuel cells for powering electronics; Journal of Materials Chemistry A; 2(43); pp. 18184-18189; Oct. 14, 2014.
Jeerapan et al.; Stretchable biofuel cells as wearable textile-based self-powered sensors; Journal of Materials Chemistry A; 4(47); pp. 18342-18353; Dec. 21, 2016.
Kim et al.; Advanced materials for printed wearable electrochemical devices: A review; Advanced Electronic Materials; 3(1); 15 pages; 1600260; Jan. 2017.
Kim et al.; Noninvasive alcohol monitoring using a wearable tatto-based iontophoretic-biosensing system; Acs Sensors; 1(8); pp. 1011-1019; Jul. 22, 2016.
Kim et al.; Non-invasive mouthguard biosensor for continuous salivary monitoring of metabolites; Analyst; 139(7); pp. 1632-1636; Apr. 7, 2014.
Kim et al.; A wearable fingernail chemical sensing platform: pH sensing at your fingertips; Talanta; 150; pp. 622-628; Apr. 2016.
Kim et al.; Wearable salivary uric acid mouthguard biosensor with integrated wireless electronics; Biosensors and Bioelectronics; 74; pp. 1061-1068; 19 pages; (Author Manuscript); Dec. 2015.
Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.
Kumar et al.; Biomarkers in orthodontic tooth movement; Journal of Pharmacy Bioallied Sciences; 7(Suppl 2); pp. S325-S330; 12 pages; (Author Manuscript); Aug. 2015.
Parrilla et al.; A textile-based stretchable multi-ion potentiometric sensor; Advanced Healthcare Materials; 5(9); pp. 996-1001; May 2016.
Windmiller et al.; Wearable electrochemical sensors and biosensors: a review; Electroanalysis; 25(1); pp. 29-46; Jan. 2013.
Zhou et al.; Bio-logic analysis of injury biomarker patterns in human serum samples; Talanta; 83(3); pp. 955-959; Jan. 15, 2011.
Zhou et al.; Biofuel cells for self-powered electrochemical biosensing and logic biosensing: A review; Electroanalysis; 24(2); pp. 197-209; Feb. 2012.
Kopelman et al.; U.S. Appl. No. 16/152,281 entitled "Intraoral appliances for sampling soft-tissue," filed Oct. 4, 2018.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
Elbaz et al.; U.S. Appl. No. 16/198,488 entitled "Intraoral scanner with dental diagnostics capabilities," filed Nov. 21, 2018.
Elbaz et al.; U.S. Appl. No. 16/188,262 entitled "Intraoral scanner with dental diagnostics capabilities," filed Nov. 12, 2018.

\* cited by examiner

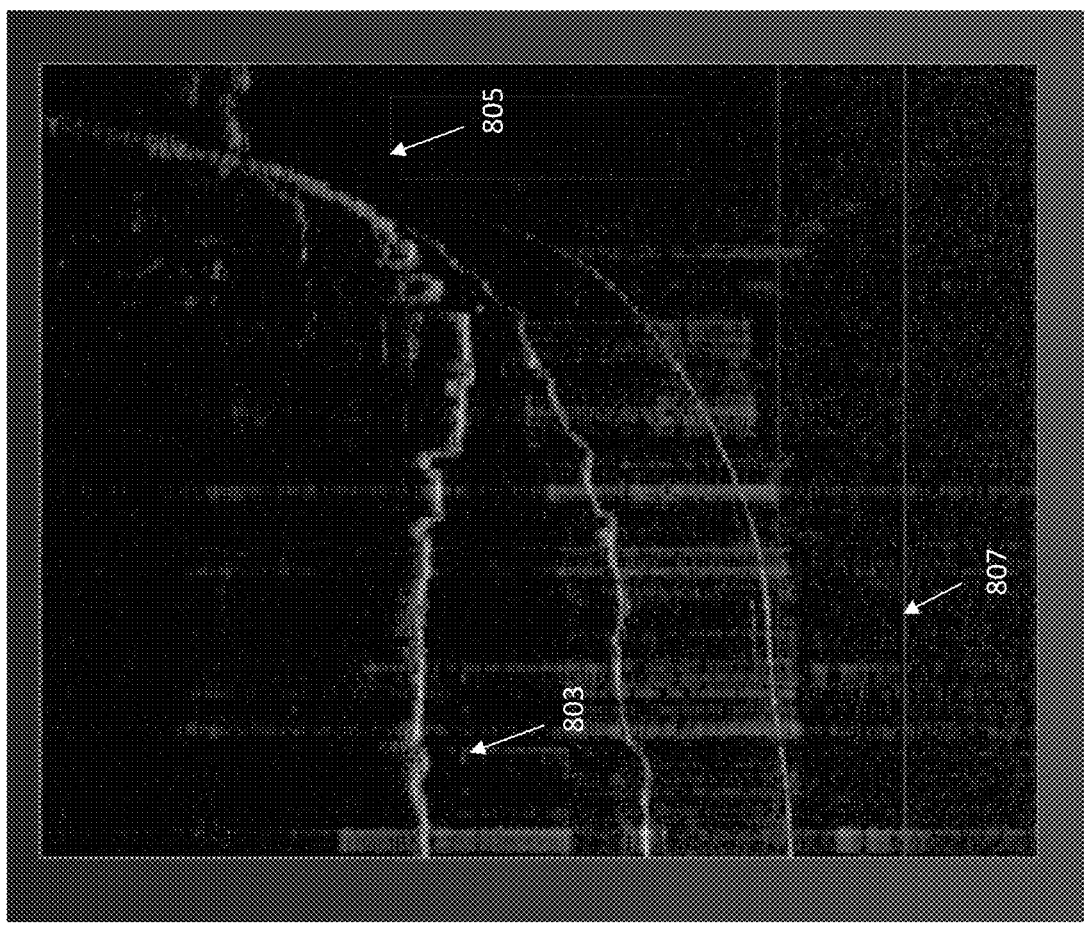

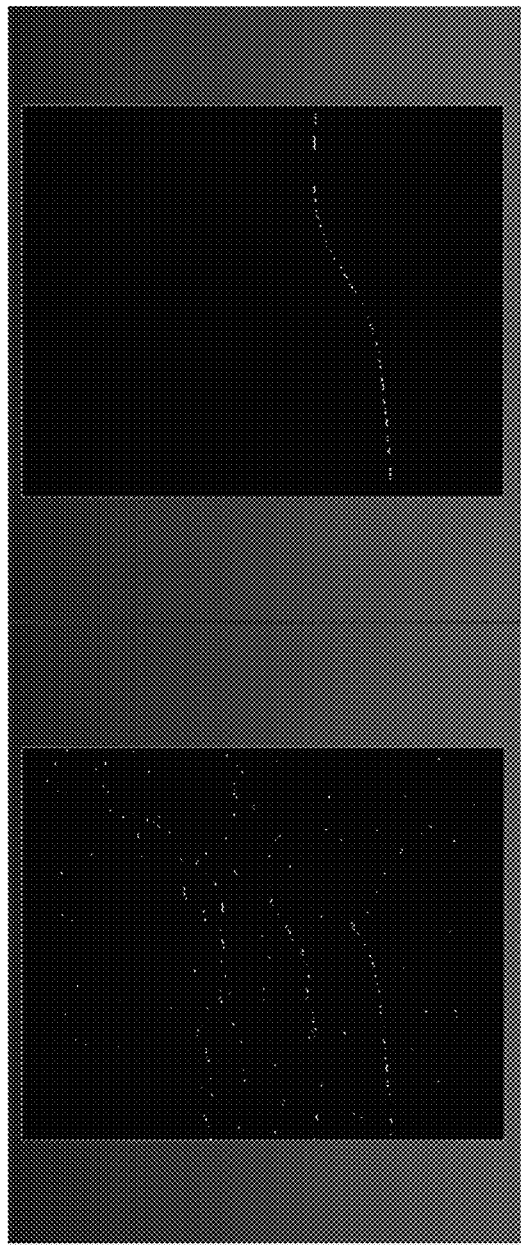
FIG. 14A
FIG. 14B
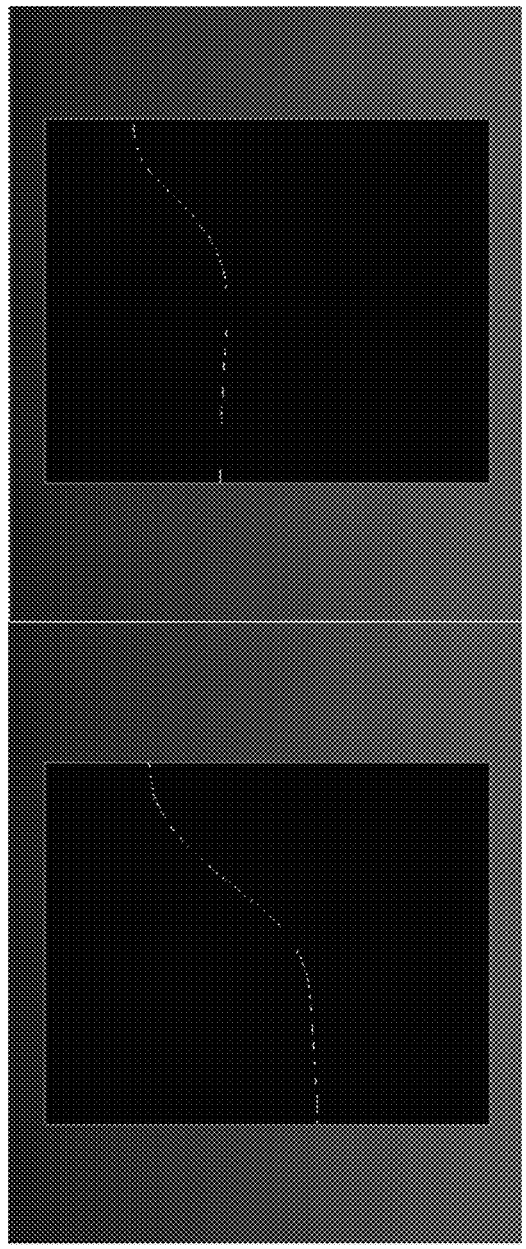
FIG. 14C
FIG. 14D

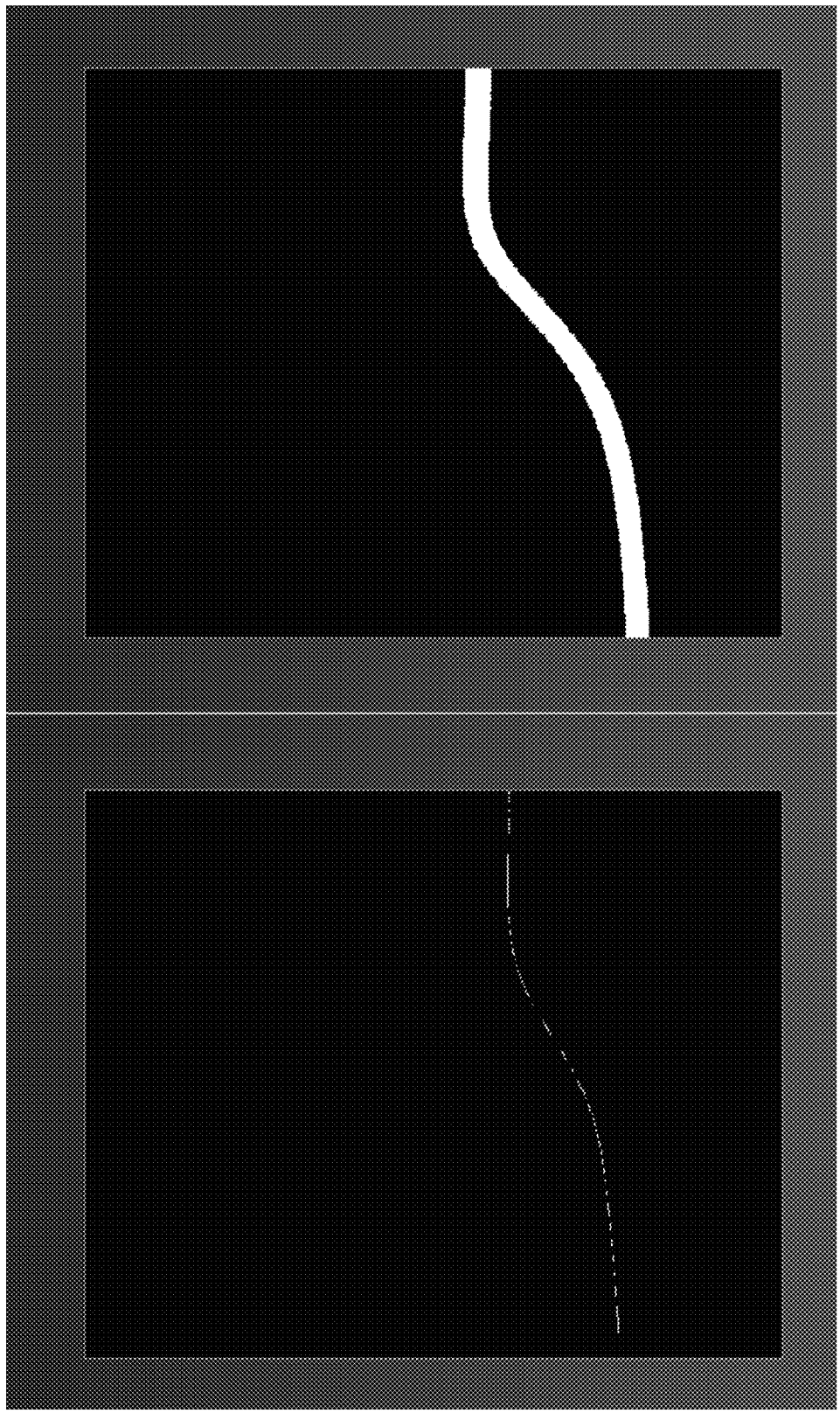

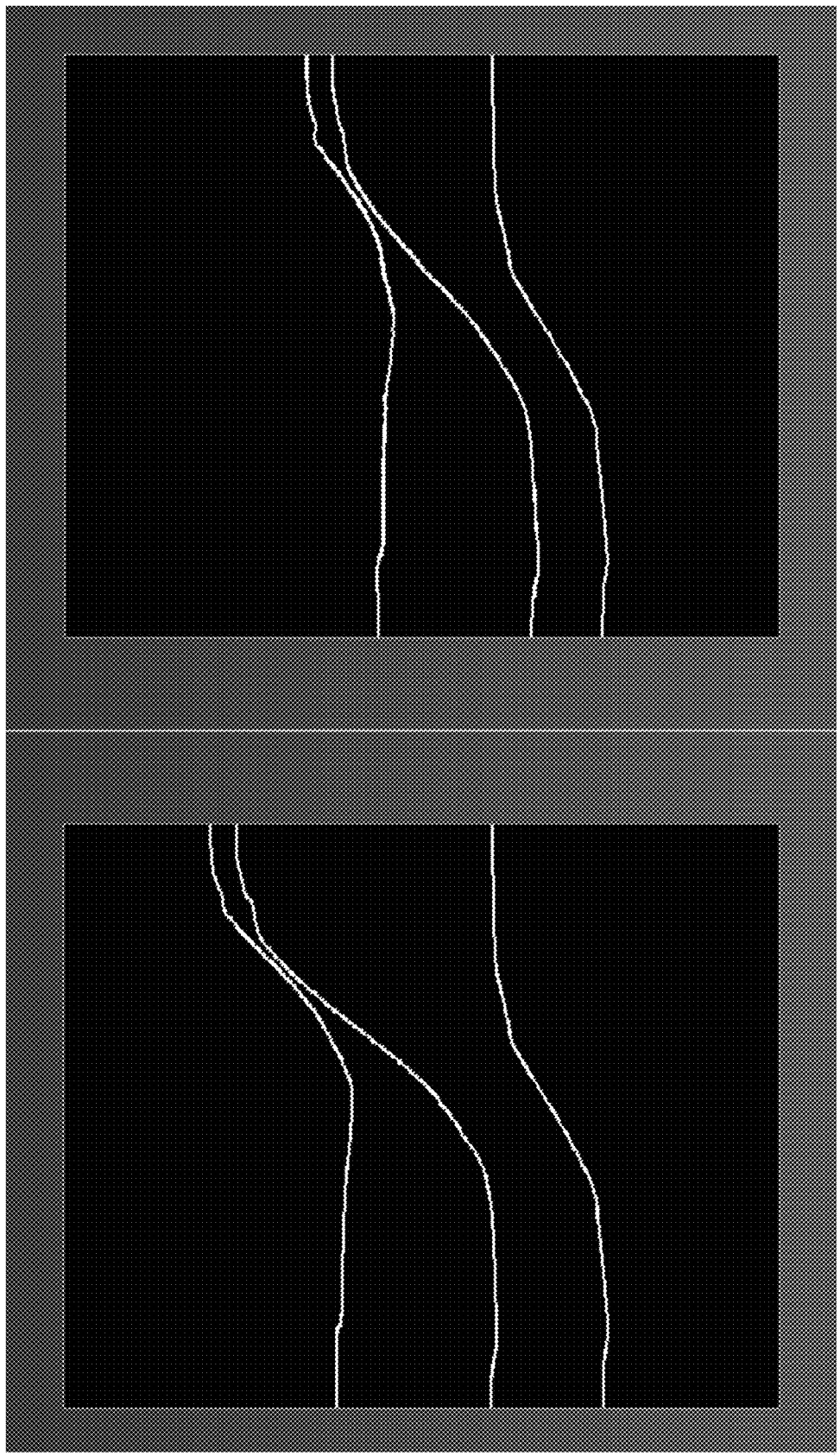

OPTICAL COHERENCE TOMOGRAPHY FOR ORTHODONTIC ALIGNERS

CROSS REFERENCE TO RELATED APPLICATIONS

This patent application claims priority to U.S. Provisional Patent Application No. 62/537,937, filed Jul. 27, 2017, and is herein incorporated by reference in its entirety.

This application may claim priority to U.S. patent application Ser. No. 15/662,234 (utility application), titled "INTRAORAL SCANNER WITH DENTAL DIAGNOSTICS CAPABILITIES," filed Jul. 27, 2017, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Dental scanning methods and apparatuses, including dental optical coherence tomography that may be used to accurately measure the geometry of an aligner and teeth simultaneously.

BACKGROUND

Many oral appliances, including dental aligners, are worn in the oral cavity and may interact with oral structures for therapeutic or cosmetic effects. For example, dental aligners are worn on the teeth to apply force to straighten the teeth. Oral appliances may be custom formed to fit the patient's teeth and oral cavity. However, measuring the fit and interaction between an oral appliance and oral structures, such as teeth, may be difficult.

Scanning may be used to examine the shape of an oral appliance or of oral structures, however it is difficult to simultaneously examine both the appliance and the teeth or other oral structures when the appliance is in place. Typical optical intra-oral scanners capture only the first surface encountered in the line of sight. The surfaces of the teeth and portions of the appliance are hidden, preventing examination of their interaction. CT scanning uses X-rays which can penetrate many materials, but with which it is difficult to simultaneously image both plastic features of a dental appliance and the teeth due to their widely different opacity to X-rays. Furthermore, these X-rays are harmful to the patient. Other techniques such as filling gaps between the appliance and the teeth with colored gels do not provide quantitative measurements and are subject to large errors and usage problems.

Thus, there is a need for methods and apparatuses that may be used to examine both an oral structure (such as the teeth) and an appliance worn on the oral structure, and particularly the interaction between the two, while the appliance is being worn by the patient. Described herein are methods and apparatuses that may address this need.

SUMMARY OF THE DISCLOSURE

Described herein are methods and apparatuses, including devices and systems (e.g., oral scanners) for concurrently imaging an oral structure (such as the teeth) and a dental appliance (such as an aligner) in a patient, while the patient is wearing the appliance, for imaging ex-vivo oral structures and appliances, or for imaging models of oral structures and appliances. These methods and apparatuses may include a scanner, or oral scanner, that includes both surface scanning and penetrative scanning. In particular, these apparatuses and methods may use penetrative scanning using an optical technique such as optical coherence tomography (OCT). Alternatively or additionally, these methods an apparatuses may include the use of a penetrative wavelength such as visible light, infrared/near-IR in trans-illumination or reflective imaging of IR/near-IR light.

Optical coherence tomography (OCT) technique was developed in the late 1980s and early 1990s and most early applications were in ophthalmology. OCT may non-invasively image through materials including some biological tissues, plastics, ceramics, and other materials, typically using near infrared light.

The complex geometry and mechanics of aligners acting on teeth may make it difficult to predict or measure the full interaction between the aligner and the teeth when an aligner is worn. OCT imaging may provide full 3D measurements of the aligner shape, positions of the teeth, locations of contact between them, and gap sizes where they are not in contact. By measuring an aligner and the teeth before and after mounting the aligner on the teeth, changes in the aligner shape and teeth positions can be observed. OCT systems normally measure only over a relatively small area capturing only one or a few teeth. Described herein are stitching techniques to join separate images together into a model of larger portions, such as a quadrant, a full jaw, or both jaws together. The resulting measurements can be used to verify aligner fit and/or locate areas of desired or undesired contact or lack of contact between the aligner and the teeth. Measurements can be made in-vivo or in-vitro. They can be used to verify the results of simulations of living jaws or laboratory models of jaws. They can also be used to evaluate the activation of attachments and the effect of staging on multiple surfaces. OCT systems can provide resolution on the order of 5 µm, fine enough that it may be used to check the accuracy of attachment shape and placement on teeth and/or the interaction between the attachment(s) and the aligner. This information may be used to modify the aligner, attachments, and/or tooth geometry to improve contacts if desired. These methods and apparatuses may also be used during manufacture of any of the apparatuses described herein. For example, an aligner manufacturer may use this information to measure the drape of plastic over a thermoforming mold to better understand the molding process and/or monitor the accuracy and consistency of the molding, or similarly to monitor other manufacturing processes such as additive manufacturing. In addition, the methods and apparatuses described herein may also be used to inspect an aligner for defects such as breaks, cracks, and/or micro-holes.

Currently, OCT may be used for inspecting the quality of dental crowns, caries, and cracks in teeth. Described herein is the use of OCT to concurrently and simultaneously measure both the teeth and an aligner. These methods an apparatuses may also scan the teeth to identify features such as cracks, caries and the like. For example, both the teeth and the aligner may be simultaneously scanned, and the scan of the teeth may be automatically, manually or semi-automatically monitored. For example, the method or apparatus may analyze the scan(s) and may alert the dental professional (e.g., dentist, orthodontist, technician, etc.) if an attachment is planned at or near a location with a cavity or crack, indicating that remedial action should be taken before installing the attachment, and/or modifying the attachment.

OCT may be used to monitor the palate. For example, OCT can image hard surfaces, including the palate. Imaging of palatal sutures could be used to monitor the results of skeletal expansion with one or more palatal expansion appliances. It is often difficult to determine when complete palatal expansion has occurred. For example, doctors typically instruct patients to continue wearing such appliances long after the desired movement has taken place, in order to ensure that new bone is bridging the gap in the suture, so that the palate won't relapse when the appliance is removed. OCT monitoring could verify that sufficient bone growth has occurred, possibly shortening the treatment time by avoiding unnecessarily extended appliance wear. As with dental aligners, the methods and apparatuses described herein may also be used to determine how well an oral appliance including a palatal expander fits onto the palate by scanning both the palatal expander and the oral cavity while the patient is wearing the palatal expander. Similarly, deformations of the appliance, the tooth positions, and the palate can be determined by comparing scans of the geometry before, during, and after use of the appliance.

The methods and apparatuses may also be used to measure, and track, features on the teeth and/or palate. For example, bony features, such as the palatal suture, could also be used as reference points when measuring tooth movements. Current intra-oral scanners typically measure the teeth and sometimes portions of soft tissues. But during orthodontic treatment, it is often the case that all of these features move, making registrations of later scans to earlier scans difficult. Features like the palatal suture typically do not change noticeably (aside from palatal expansion treatments), thus, they can provide a reference for proper registration of images spaced in time. In some variations one or more fiduciary markers may be anchored to the teeth and/or to the palate. For example, scanning targets (e.g. temporary anchoring devices, or TADs) may be applied to the patient for this purpose, e.g., by a dental professional (e.g., dentist, orthodontist, etc.). This may allow imaging of bony structures even if the soft tissues over them are too thick for a reliable OCT signal imaging of the bone. The scanning target may be rigidly attached to a bony structure such as the palate, and may therefore reflect the position and/or orientation of the body structure between scans.

Data from 3D scanning of aligners on patients may be collected and used to form a database; this database may include outcomes and treatment commentary, and may be used as a resource in treatment planning and aligner design.

The direct measurement of tooth displacements when the aligner is being worn also may permit the prediction of tooth movement direction as the bone remodels. A patient's treatment plan may be modified by comparing a desired tooth movement, final and/or intermediate tooth positon with predictions made by examining the predict tooth movement (including rotation) as determined from the combined aligner/tooth scans. To the extent that the predicted linear or rotational displacements are not aligned with the desired vectors, this information may be used to modify a treatment plan.

Although the examples described herein are specific to OCT, any of these methods may be performed with CT scanning, despite the risk of X-ray exposure, e.g., by providing appropriate shielding.

As discussed above, any of the methods and apparatuses described herein may include can the patient with a dental appliance (e.g., an aligner) mounted in place. Any of these methods and apparatus may also be configured to build a 3D model of all the spaces between the aligner to the dentition. For example, the method may be configured to index or allow a user to select display and/or quantification of spaced between the aligner and the patient's dentition. In some variations, the apparatus or method may allow the user to select areas of contact (e.g., actual contact) between the appliance, e.g., aligner, and the teeth.

The apparatuses described herein may be configured to determine the boundary between the appliance (e.g., aligner) and the patient's dentition by any appropriate method, including, for example, by segmenting the 3D model. When OCT is used to generate images through the teeth and aligner, for example, the resulting images may be combined and used to form a 3D volumetric model of the teeth and aligner. This model may be segmented to identify separate regions. Segmentation may include direct segmentation of the penetrative images. This may allow for the identification of dentin within the teeth, including the location and morphology of the dentin, the identification of the aligner, as well as the identification and location of cracks, lesions, and/or caries in the teeth, including in the dentin. The use of segmentation may allow for reconstruction of a volumetric model based on the penetrative images and the knowledge of the camera position corresponding to the penetrative images. A volumetric model of teeth can be segmented and these segments (relating to different internal structures of the tooth and/or aligner) may be projected back to the images.

The segmentation can be done on 2D images or on volumetric models. The segmentation can be used to classify the images and/or the 3D models according to the presence of different segments. A user may be able to detect by this segmentation manually or automatically (or semi-automatically) to classify different internal structures. Further, the images or models may be used to measure internal regions of an aligner or tooth/teeth, or the regions between them.

As described herein, any of the methods and apparatuses described herein may also include the outputting (via display or otherwise) of an estimate of the magnitude and direction of the force at the points of contacts of the teeth based on one or more of the size of the area of contact and/or the direction of the force, based on the distortion of the shape of the aligner (e.g., relative to shape before mounting).

The information derived and/or presented may be used as part of a dental procedure, for example, to indicate to the dental practitioner how to modify the appliance, such as the aligner. For example, this information may be used to indicate where on an aligner to make holes or dimples in order to change the force system. Alternatively the apparatus may use this information to recommend designing a new aligner.

In any of these methods, as described herein, the appliance (e.g., aligner) may be scanned before mounting to the patient's teeth and/or the teeth may be scanned before mounting the appliance. Thereafter, the mounted (worn) appliance may be scanned, and the resulting models may be compared to calculate the distortion and check virtually if it seated well and likely to function. Areas that are likely disengaged may be indicated.

In any of these methods one or both models may be adjusted or normalized for direct comparison/subtraction. For example, one or both 3D volumetric models of the aligner, teeth and/or teeth and aligner may be morphed by using the teeth or other region(s) to compare and adjust the one or more models; the models may also be aligned. For example, described herein are methods in which the aligner is scanned before mounting and a volumetric model of the aligner is generated. Thereafter a volumetric model of the aligner may be generated after mounting. The apparatus or method may then find areas that were "stretched" and the resulting force generated from this stretch.

In some variations, teeth may be scanned before mounting, and then the teeth may be scanned after the mounting (e.g., thru the aligner). This may be used to demonstrate the immediate new teeth arrangement due to the aligner, and may also demonstrate which teeth have moved in to what direction. The resulting scans (which, as in any of these examples, may be a 3D volumetric model, a series or set of 2D images, a panoramic image, etc.) may be analyzed to determine if the system generated proximal contacts that may stop wanted movements.

Also described herein are methods of determining fit and/or efficacy of a retainer, e.g., worn following a dental procedure such as alignment. In this example, the teeth may be scanned while the patient is wearing the retainer at different time points. Comparison across time may allow the system to determine if the patient's teeth are passive or static (e.g., not moving).

Any of the methods and apparatuses described herein may also be used to determine the sufficiency of or otherwise analyze the spaces left in the oral cavity for teeth to erupt. For example, any of these methods may be used to analyze or determine contacts between teeth (e.g., spacing) and report if it eliminates the planned movement.

For example, described herein are methods of processing a dental aligner, and apparatuses for performing the methods. Processing may include modifying, imaging, adjusting, analyzing, reviewing, fitting, etc. For example, a method of processing a dental aligner may include: scanning, using an optical coherence tomography (OCT) scanner, a patient's teeth while a dental aligner is worn on the teeth, wherein scanning comprises scanning both the dental aligner and the patient's teeth together; generating a three-dimensional (3D) model of the combined dental aligner and patient's teeth; and displaying, storing and/or transmitting the 3D model.

Scanning may comprises scanning a plurality of 3D volumes each comprising a set of voxels corresponding to the aligner and teeth.

Generating the 3D model may comprise stitching the plurality of 3D volumes. In some variations, generating the 3D model comprises filtering the 3D volume to remove noise prior to stitching the plurality of 3D volumes. Any of these methods may include binarization of greyscale 3D volume intensity by identification of local intensity maximums for each Z-section.

Any of these methods and apparatuses may include parsing the plurality of 3D volumes to isolate an aligner outer surface, an aligner inner surface and a tooth surface. Parsing may also optionally identify regions of contact (e.g., collision or contact within a predefined distance). Any of these methods may also include determining or estimating an optical property of the material being imaged and adjusting the geometry of the 3D model based on the optical property.

Any of these methods and apparatuses may also include smoothing each of the aligner outer surface, the aligner inner surface and the tooth surface. In some variations, these method may include correcting an optical path length of the plurality of 3D volumes after isolating the aligner outer surface, the aligner inner surface and the tooth surface.

Scanning may include scanning in the near-IR wavelength using the OCT scanner. In any of these apparatuses and methods, displaying, storing and/or transmitting the 3D model may include displaying the 3D model in real time. Any of these methods may further comprising detecting regions of contact between the aligner and the patient's teeth from the 3D model; and/or determining gaps between the aligner and the patient's teeth, including gaps above a predetermined threshold (e.g., greater than 0.2 mm, 0.5 mm, 0.8 mm, 1 mm, 1.1 mm, 1.2 mm, etc.). For example, these methods or apparatuses may detect gaps between the aligner and the patient's teeth from the 3D model, and/or may display, on the 3D model, the detected gaps.

Any of these methods and apparatuses may also display, on the 3D model, the detected region of contact (and/or gaps).

The methods and apparatuses described herein may also or additionally estimate forces acting on the patient's teeth by the aligner using the detected region of contact.

A method of processing a dental aligner (e.g., imaging, fitting, correcting, adjusting, applying, etc.) may include: scanning, using an optical coherence tomography (OCT) scanner, a patient's teeth while a dental aligner is worn on the teeth, wherein scanning comprises scanning both the dental aligner and the patient's teeth together; generating a three-dimensional (3D) model of the combined dental aligner and patient's teeth; identifying regions of contact between the dental aligner and the patient's teeth; and displaying the regions of contact.

In any of these methods or apparatuses, displaying may comprise interactively displaying, comprising allowing the user to rotate and/or zoom into the view. For example, displaying may comprise displaying a 3D model of the patient's teeth with the regions of contact indicated thereon.

Any of these methods may include modifying an orthodontic treatment plan including the aligner based on the regions of contact. For example, a treatment plan may be modified by adjusting the amount or type of movement, the location or orientation of one or more attachments, etc.

In any of these methods, the patient's teeth may include one or more attachments, and identifying regions of contact between the dental aligner and the patient's teeth may comprises identifying regions of contact between the dental aligner and the one or more attachments. Any of the methods and apparatuses described herein may focus on the attachments, including the interaction between the aligner and the attachments.

In general, displaying may comprise displaying in a user interface accessible to a dental practitioner.

As mentioned, also described herein are systems configured to perform any of the methods described herein. For example, a system for imaging a dental aligner may include: an optical coherence tomography (OCT) scanner; one or more processors; a memory coupled to the one or more processors, the memory configured to store computer-program instructions, that, when executed by the one or more processors, perform a computer-implemented method comprising: scanning, using the OCT scanner, a patient's teeth while a dental aligner is worn on the teeth, wherein scanning comprises scanning both the dental aligner and the patient's teeth together; generating a three-dimensional (3D) model of the combined dental aligner and patient's teeth; identifying one or more regions of contact between the patient's teeth and the dental aligner from the 3D model of the combined dental aligner and teeth; and displaying the one or more regions of contact.

Any of the methods and apparatuses described herein may be modified for use to observe, measure and/or treat a palatal region, e.g., for palatal expansion. For example, the methods descried herein may be configured as methods of processing (e.g., imaging) a palatal suture, and may include: scanning, using an optical coherence tomography (OCT) scanner, a patient's palatal region while a dental appliance is worn on the palate, wherein scanning comprises scanning both the dental appliance and the patient's palate; generating a three-dimensional (3D) model of the combined dental appliance and patient's palate; and identifying separation of the palate. Identifying the separation of the palate comprises identifying the rate of separation of the palate.

Also described herein are methods of making, modifying, adjusting or revising an orthodontic treatment plant (e.g., a dental plan) for aligning a patient's teeth. For example, the method may include: scanning the patient's teeth while a first dental aligner is worn on the teeth, using an intraoral scanner configured to record optical coherent tomographic (OCT) images, wherein scanning comprises scanning both the first dental aligner and the patient's teeth together, wherein the first dental aligner has a first design; generating a three-dimensional (3D) model of the combined first dental aligner and patient's teeth; identifying one or more of: thicknesses of the dental aligner in a plurality of regions, and regions of contact and/or gaps between the first dental aligner and the patient's teeth using the 3D model; and adjusting the first design of the first dental aligner to form a second dental aligner based on the one or more of: the thicknesses of the dental aligner in the plurality of regions, and regions of contact and/or gaps between the first dental aligner and the patient's teeth.

Any of these methods may also include estimating forces acting on the patient's teeth using one or more of: the identified regions of contact, deformation of the dental aligner, and/or the thicknesses of the dental aligner. The method may also include estimating a change in the shape, thickness or both of the aligner based on the 3D model. Generating the 3D model may include marking the 3D model to show one or more of: regions of contact, gaps, thinner regions of the aligner, etc. Adjusting the design may comprise adjusting the thickness and/or position of a wall of the first dental aligner to form the second dental aligner. The methods may include forming the second dental aligner by one or more of: thermoforming and 3D printing.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6A shows a raw OCT scan section in which interface surfaces for each of the tooth, aligner outer and aligner inner surfaces are visible and have been marked. FIG. 6B shows a histogram of 1D optical reflective light intensity from the 2D section of FIG. 6A, indicating that these three primary surfaces correspond to the three highest peak intensities. FIG. 6C illustrates an initial surface identification using the intensity values.

FIG. 8 illustrates one example of a section through an OCT scan (e.g., a z-section through the voxel data of the OCT scan), showing raw data, including various noise and artifacts.

FIGS. 14A-14D illustrate additional operation of a parser of a voxel mapper, showing identification of each of three surfaces in the OCT scan data volume. FIG. 14A shows a section through a filtered volume; FIG. 14B shows a section through an isolated first surface within the volume; FIG. 14C shows a section through an isolated second surface within the volume; and FIG. 14D shows a section through an isolated third surface within the volume.

FIGS. 15A-15B illustrate smoothing and cleaning of one of the isolated surfaces implemented by running a diffusion simulation using white points as a power sources. FIG. 15A is a section through an isolate surface within the volume prior to smoothing, and FIG. 15B shows the same surface following smoothing.

FIGS. 17A-17B illustrate adjusting the optical path length of the volume including all three of the surfaces identified, isolated and processed in FIGS. 12A-16B. A section through the volume showing all of the surfaces combined is shown in FIG. 17A; FIG. 17B shows the same volume after correcting for the optical path length (e.g., based on the known or expected indexes of refraction through the aligner, air and/or teeth).

DETAILED DESCRIPTION

Figure 1:
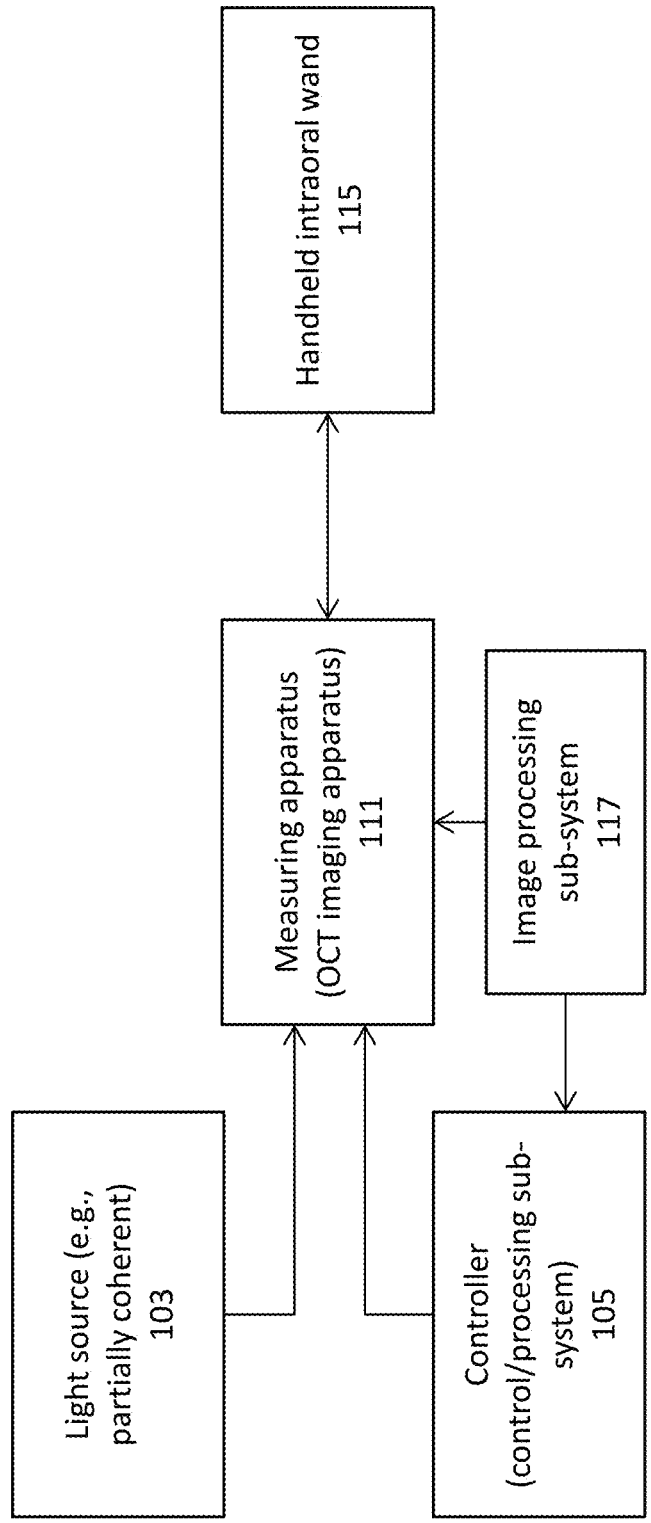
FIG. 1 schematically illustrates an intraoral scanner configured to measure OCT.

Optical coherence tomography (OCT) uses a beam of partially coherent light to create tomographic images. There are two basic types of optical coherence tomography: time domain optical coherence tomography and Fourier domain optical coherence tomography. Time domain OCT was developed in 1991 for use in ophthalmic diagnosis. It can produce tomographic images of relatively low quality, resulting from long time of measurement, but it does not readily allow for three-dimensional imaging of objects. Modern optical tomography with detection in the frequency domain (Fourier domain optical coherence tomography) reduces the capture time by more than a hundred times and may be used to create three-dimensional images of the object.

Optical coherence tomography enables the visualization into a volume, and may be used with any wavelength of electromagnetic radiation. It is practical for visible light and near infra-red (Near IR or NIR) wavelengths, though other wavelengths are also possible. Most commercial systems are tuned for NIR, which allows penetration a small distance into biological tissues such as the retina and teeth, however it should be understood that the methods and apparatuses described herein may be used with any wavelength. In particular, when imaging dental appliances such as aligners as described herein, visible light may be used, and may provide high resolution due to the shorter wavelength of visible light (e.g., compared to NIR). In the OCT scanner based systems and methods described herein, the information about the location of scattering (reflecting) layers along the sample beam may be contained in the modulation frequency of the light intensity measured as a function of frequency. The electric signal resulting from detection of spectra of interfering beams is called the signal of spectral bands. Two methods of practical realization of this type of detection may be used. The first is spectral optical coherence tomography (SOCT). The other method is swept source OCT or optical Fourier domain imaging (OFDI). The common elements, used in both methods (SOCT and OFDI), are fixed reference mirrors (as opposed to time domain OCT). This improves mechanical stability of the system. An interference image is obtained by the numerical Fourier transform of registered spectral bands. However, the method of detection of an interference signal is different. In SOCT, the light source generates a broadband light beam. A spectrometer is used to detect signals for individual optical frequencies. In OFDI, an ordinary photodetector is used instead of a spectrometer, because the applied fast tunable laser generates light of a narrow spectral line individually for each wavelength. SS-OCT uses a short cavity swept laser with a tunable wavelength of operation instead of the diode laser used in spectral-domain OCT.

OCT consists of coupled hardware components, and may include software. The hardware, software, and/or firmware may include: a partially coherent light source, an imaging apparatus, a measurement head, a module of data processing, and image generation as well as a computer control system. The light source used may determine its axial resolution and penetration depth of the light beam. The OCT imaging apparatus module may be any measuring device capable of measuring the reflected or backscattered light with high sensitivity and resolution. Other elements of the OCT system may include the measuring head and a system for bringing the probe beam to the intraoral cavity. Analysis of the obtained values, their processing, and presentation may be achieved through a variety of image processing techniques, such as noise reduction algorithms, motion and visualization correction algorithms, segmentation, and image resolution enhancement.

The computer control system may control the entire OCT scanner, and enable control of scanning the reference arm of the interferometer and synchronize the operation of all components. Moreover, it may allow for communication between the apparatus and the image processing block as well as the display of measurement results in real time. An example of this is shown in FIG. 1. In FIG. 1, the schematic for an intraoral scanner including OCT imaging includes a light source (e.g. partially coherent light source 103), a controller 105 (e.g., processor for computer control of the apparatus), an OCT measuring apparatus 111 (which may include an interferometer), and a hand-held scanner head/wand 115.

OCT imaging is possible by measuring the intensity and time delay of the "echo" of the reflected or backscattered light. The method of OCT imaging is analogous to ultrasonography. The distance measured by OCT is characterized by a much higher time resolution than ultrasound. OCT resolution may be as fine as 5 µm (compared to 150 µm in ultrasound). OCT may penetrate to a depth of, e.g., 5 mm, depending on the material being scanned. It should be noted that the methods and apparatuses described herein may also or alternatively be adapted for use with ultrasound. Optical tomography is based on the phenomenon of interference of two partially coherent light beams coming from a single source, a reference beam and a probe beam, or in common path OCT, the reference beam may be directly derived from the probe beam. The analysis of interference signal enables the system to locate the points at which the refractive index changes. These points may be situated along the direction of propagation of the probe beam. The reflected wave power density may be a function of the position of the reflective point, which is the source of the wave, and may be referred to as an A-scan. B scans give sagittal scans of the object and C scans may provide lateral scanning images at a constant depth. Combinations of measurement results lying in one plane (e.g., numerous parallel directions of the probe beam) may be used to create a two-dimensional image of the section of the test object.

Boundaries may be determined by layers with different refractive indices (e.g., the refractive index changes as a function of light beam penetration depth) which may be determined by interferometric distance measurement systems.

When imaging the teeth, OCT may be used to image caries, caries incipiens, and cracks in enamel. Soft tissues may also be visualized, including the gingiva, periodontal ligaments (before and during orthodontic tooth movement), etc.

To maximize the efficiency of the dental diagnostic OCT, the wavelengths of light chosen for generating the image may be one that images at least the boundaries of the aligner and the teeth. Light within the near infrared light range may be used. The central wavelength may determine the maximum depth of penetration into the tissue due to scattering and absorption properties. In addition, the material forming the dental appliance (e.g., aligner) may be selected or treated to permit visualization under the wavelength of OCT that is chosen (e.g., within the near-IR range used).

Figure 2A:
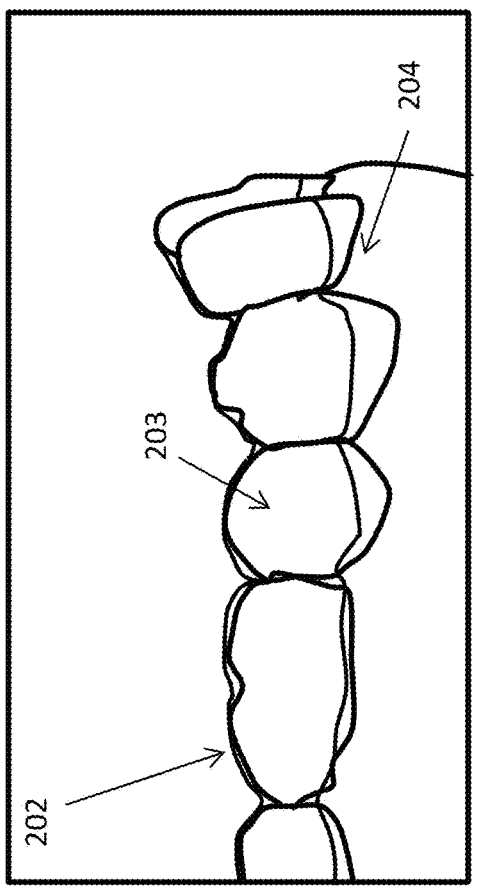
FIG. 2A illustrates a patient's teeth wearing an aligner.
Figure 2B:
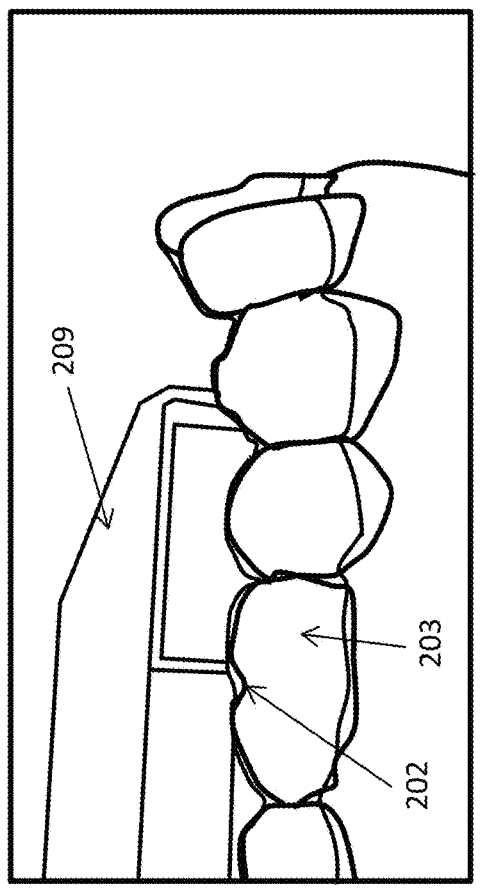
FIG. 2B shows an intraoral scanner imaging the aligner worn on the teeth.

FIGS. 2A and 2B illustrate one example of a method of using an intraoral scanner configured to take OCT images of a dental aligner being worn on a subject's teeth, and reconstructing a three-dimensional model of the combined aligner/teeth so that interactions between the two maybe examined. FIG. 2A illustrates a dental aligner 202 worn on a patient's teeth 203. Soft tissue, such as the gingiva 204 is also shown. In FIG. 2B, an intraoral scanner 209, configured for OCT is shown scanning both the dental aligner and the teeth.

By scanning the dental aligner worn on the teeth, the apparatus may generate images showing the interaction between two. For example, a 3D representation (images, models, etc.) of the aligner and teeth may be generated, or one or more series of 2D images. These images or models may be analyzed, including automatically or manually analyzed, to identify interactions and/or interference between the two.

Figure 3:
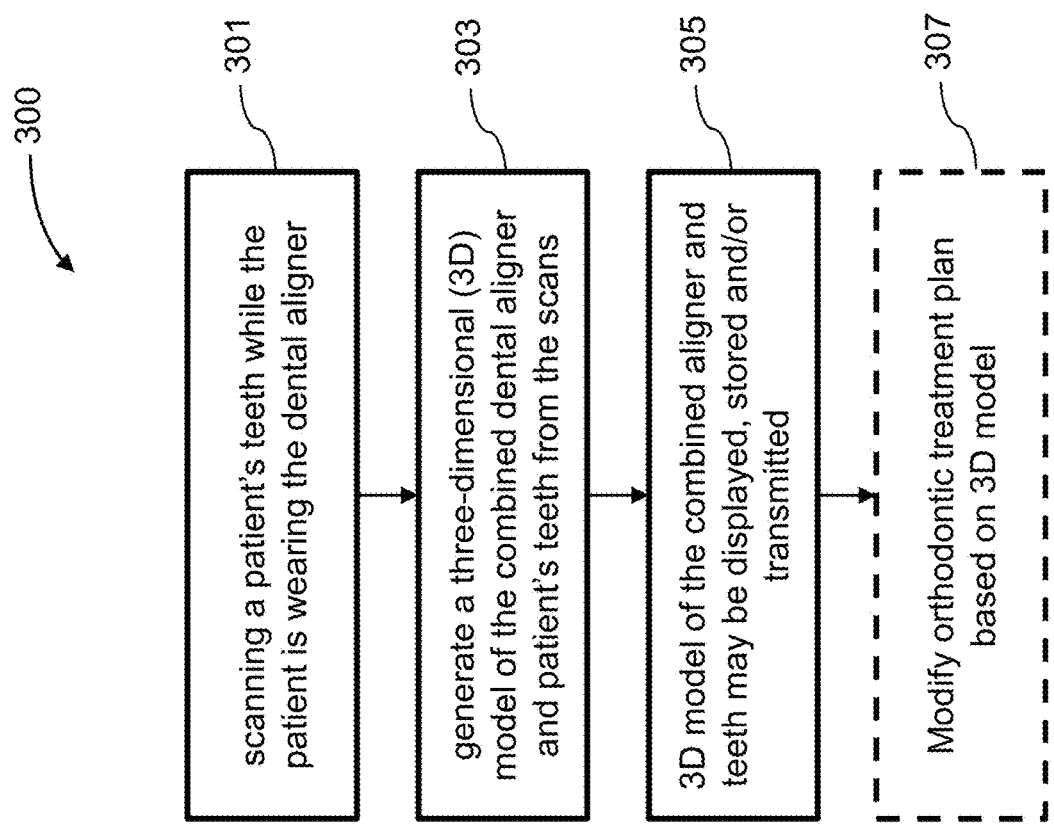
FIG. 3 is a diagram illustrating a method including imaging an aligner while worn on a patient's dental arch.

For example, the methods described herein may include a method of imaging a dental aligner. FIG. 3 illustrates one method of imaging the combined aligner and teeth. These methods may include first scanning a patient's teeth while the patient is wearing the dental aligner 301, using an intraoral scanner configured to record optical coherent tomographic (OCT) images. The aligner may be properly seated on the teeth, as it would be when worn by the patient. Either the patient or the dental practitioner may seat the aligner on the teeth. The patient may be asked to bite down, to ensure that the aligner is seated. Alternatively, the aligner may be scanned on a model or imprint of the subject's teeth.

The resulting scans will include a combined scan of both the dental aligner and the patient's teeth, together. The scans may then be analyzed by the processor (e.g., image processor) to generate a three-dimensional (3D) model of the combined dental aligner and patient's teeth 303. This step may include combining (e.g., stitching together) the scans to form a complete 3D model. Image stitching in this way may be done using known image processing techniques. Sequential scans may be registered, averaged and one or more surface meshes may be generated.

The 3D model of the combined aligner and teeth may be displayed, stored and/or transmitted 305 (e.g., for further processing). Displaying, storing and/or transmitting the 3D model may comprise displaying the 3D model in real time. For example, the 3D model may be displayed in real time, allowing the dental practitioner to "fill in" the 3D model in real time with the intraoral scanner. The displayed image may be marked (e.g., by color, text, flags, etc.) to show regions that are not sufficiently well scanned and/or to show any other features (including contact, etc.).

The 3D model may be analyzed after and/or during scanning. For example, the 3D model may be examined to determine the forces acting on the patient's teeth based on the 3D model. Force may be estimated, for example, by examining the thickness of the aligner when worn on the teeth to the "relaxed" thickness, which may be known (e.g., for aligners fabricated to have a uniform and/or known thickness, e.g., by 3D printing). Alternatively or additionally, force may be estimated by monitoring a marker for force on and/or in the aligner. A finite element simulation of the aligner system may be made and the OCT information may be used to obtain the initial geometry for input to the simulation. The final geometry of the aligner when worn on the patient's teeth (or a model of the teeth) may be obtained and this final geometry may be used to verify the results of the simulation.

In some variations a scan of the aligner may be made when the aligner is not worn, and the change in thicknesses (and/or positions of sub-regions of the aligner) may be identified to determine the forces acting on the aligner. Thus, any of the methods described herein may determine the thickness of the aligner from the 3D model. The forces may be modeled using the 3D data and including constrains of the material properties and/or geometry of the aligner, which may be known. Further, the forces may be absolute or relative. Force diagrams (including thermal plots showing regions of high/low forces) may be generated using the 3D model of the aligner and teeth, or just a 3D model of the patient's teeth, which may also be scanned separately.

Any of these methods may determine/detect regions of contact between the aligner and the patient's teeth from the 3D model. These regions of contact may be detected by directly analyzing the 3D model, to identify close proximity between the surface of the aligner and the dental surface, which may be distinguished using OCT. As mentioned, the 3D model may be used to display the contact regions. In any of the display variations described herein, the resulting analyzed data (e.g., force, contact, gaps, etc.) may be shown on the 3D model including both the aligner and teeth, e.g., with the aligner and/or teeth shown semi-transparent and the highlighted component (e.g. force, region of contact, gaps, etc.) colored, etc.; alternatively or additionally, the 3D model may be manipulated to remove one of the aligner (showing just the teeth) and/or the teeth (showing just the aligner); in some variations a separate scan of just the aligner and/or just the teeth may be performed and may be combined with the 3D OCT scan (any of the 3D scans above may be 3D "OCT" scans, e.g., taken with optical coherence tomography). For example, in some variations the combined aligner and teeth scan may be combined with a scan (e.g., an OCT scan, a surface scan, or other scan modality) of the patient's teeth. The two 3D scans may be placed in registration. Such dual or combined scans may be particularly useful to show features in, on, or within the teeth.

In some variations, a teeth-only scan may be performed prior (e.g., immediately prior, shortly before, etc.) using the same intraoral scanner, using OCT or any other imaging modality (e.g., visible light, etc.). The intraoral scanner may be used to aid in taking the combined teeth and aligner scan, and may be displayed while scanning the combined scan, so that the aligner maybe filled in as the combined OCT scans are acquired.

As mentioned, the 3D scan (e.g., 3D OCT scan of both the teeth and the aligner) may be used to detect gaps between the aligner and the patient's teeth. For example, the surface of the aligner and/or the surface of the teeth may be identified from the OCT scan (or, as mentioned above, from a hybrid OCT and other scan, e.g., surface, scan). Any of these methods may include displaying, e.g., on the 3D model, the detected gaps.

As shown in FIG. 3, the 3D scan may then be used to modify the orthodontic treatment plan 307. For example, the treatment plan may be modified by revising the design of the aligner to better fit the patient, e.g., if the gaps and/or contact mapping shows an ill fit between the aligner and the teeth. The treatment plan may be modified by adjusting the forces acting on the aligner. For example, the distribution of forces acting on the teeth by the aligner may be estimated as described above, e.g., based on the thickness and/or contact points/surfaces. This information may be used to model the movement of the teeth using the scanned tooth position or a separate scan of the patient's teeth alone, and compared to the final (or an intermediate) desired position.

Thus, also described herein are methods of correct, adjusting or revising a dental treatment plan. These methods may also be referred to as methods of making a dental aligner. These methods may include: scanning, using an intraoral scanner configured to record optical coherent tomographic (OCT) images, a patient's teeth while a first dental aligner is worn on the teeth, wherein scanning comprises scanning both the first dental aligner and the patient's teeth together, wherein the first dental aligner has a first design. The scans may generate (e.g., in real-time) a three-dimensional (3D) model of the combined first dental aligner and patient's teeth. As mentioned, in any of these variations the 3D model may be combined with or displayed overlapping with a prior 3D model of just the subject's teeth. Once scanned, or during the scan, the apparatus may identify regions of contact and/or gaps between the first dental aligner and the patient's teeth using the 3D model (optionally). Finally, the design of the first dental aligner (the "first design") may be adjusted or modified to form a second dental aligner or series of dental aligners having a second design. This process may be based on the 3D scan, and the analysis of this data, including one or more of: the identified regions of contact and/or gaps, and/or the thickness of the dental aligner when worn.

As discussed above, the forces acting on the subject's teeth may be estimated from the 3D images, e.g., from a change in the geometry of the dental aligner when it is worn on the teeth compared to the thickness of the aligner when it is not being worn. As mentioned, this unworn (or relaxed) thickness and/or shape may be known a priori from the material or fabrication technique (e.g., 3D printing and/or thermoforming) or it may be determined by scanning the aligner in the unworn configuration and subtracting, and/or it may be used as part of a finite element analysis to match predicted changes in the geometry to solve for the forces on the aligner(s). The forces acting on the teeth may be reflected in the compression (e.g., change in geometry) of the aligner. In some variations, the forces on the aligner may be estimated and used to project onto the patient's teeth (or a digital model of the patient's teeth). The distribution of forces on the teeth may thus be based on the OCT imaging data received from the aligner. Alternatively and/or additionally the force distribution may be approximated from the region of close contact, presumably acting to apply forces, directly visualized by the OCT imaging of the aligner on the patient's teeth and/or a model of the patient's teeth.

The modification of the first design may include modifying (from the first design) one or more of the: thickness and/or position of a wall of the first dental aligner to form the second dental aligner. The new aligner or series of aligners may be formed by any appropriate method, including directly 3D printing of the new aligner(s), or of a model of the teeth adjusted to account for the changes, over which a new aligner may be thermoformed.

Examples

An OCT system may be used for scanning an aligner, or each aligner of a series of aligners, on a patient's teeth, in order to examine the aligner fit and the interaction with the patient's teeth. In some variations the OCT system may scan the patient's teeth and aligner directly, e.g., within the patient's oral cavity. In some variations, the OCT system may scan the patient's teeth and aligner indirectly, by scanning the aligner worn on a model (e.g., a cast) of the patient's teeth. In any of these variations, images of the aligner worn on the patient's teeth may be taken (recorded) for later analysis and/or analyzed immediately.

The scanning system may scan for a variety of fields of view (e.g., dimensions of the scanning field) and/or for various times. Scanning resolution may be, for example, between 1 and 100 microns (e.g., between 2 and 50 microns, between 5 and 30 microns, between 6-10 microns, between 6-30 microns, between 6-50 microns, etc.). As mentioned above, any appropriate wavelength may be used for the OCT, including visible and near-IR wavelengths. For example, in some variations the illuminating wavelength may be between 1000 and 1400 nm (e.g., between 1200 and 1350 nm, between 1250 and 1350 nm, between 1300 and 1320 nm, etc.).

In some variations an OCT apparatus (such as that shown and described above in reference to FIG. 1) may include an OCT scanning laser that operated within a predetermined wavelength or range so wavelengths. For example, the OCT scanning laser may be a 16 MHz laser, a 30, 50, 100, 200 MHz laser, etc.

The field of view may be, for example, a 5 mm×5 mm×6 mm volume; multiple volumes may be scanned and digitally connected (stitched) to form a volume of the patient's teeth and/or dental appliance. For example, depth of view may be from about 5 mm to about 20 mm.

For example in some variations an aligner (or a series of aligners) may be examined while worn on a patient's teeth by scanning, using optical coherence tomography, a model of a patient's teeth on which an aligner is worn. The scan may be a digital (or digitized scan) showing the interface between the aligner and the teeth. The scan may be used to generate a volumetric model either directly or by combining with a volumetric model of the patient's teeth and/or aligner. The OCT scan, including a volumetric OCT scan, may be used to analyze the aligner fit. In some variations, the OCT scan(s) may be used to identify where on the patient's teeth force(s) from the aligner is being applied to patient's teeth. For example, the distance between the aligner and the teeth may be determined from the OCT scan. This may allow visualization of where the force is being applied to the teeth and may also allow confirmation of the force system on the aligner during an orthodontic treatment. Tooth contact information may include both information about where on the aligner the teeth are contacting as well as where the teeth are not contacting.

In some variations the OCT imaging information on contact location may be correlated with expected tooth contact information. For example, the method or system may be configured to extract the actual contact information and compare this to expected tooth contact information based on a treatment plan. In some variations the actual tooth contact data from the OCT imaging information may be used to confirm tooth contact during orthodontic treatment and/or to modify or adjust an orthodontic treatment plan.

In any of these variations, the methods may also be used to visualize the movement of the patient's teeth. For example, acute movements may be visualized (e.g., up to 0.5 to 1 mm, such as about 0.25 mm of tooth movement) immediately after attaching the aligner to the patient's teeth (particularly when intraoral imaging). The use of OCT may allow very high resolution imaging, and may also be sufficiently time resolved to see both acute and longer-term movements. For example, scans prior to placing the aligner on the teeth may be taken (e.g., immediately prior to wearing the aligner) and/or immediately after attachment, and scans of the same region(s) taken at various times after applying the aligner to the teeth (e.g., 5 minutes after, 10 minutes after, 20 minutes after, 40 minutes after, 1 hour after, 1.5 hours after, 2 hours after, 3 hours after, 6 hours after, 12 hours after, 1 day after, 2 days after, 3 days after, 4 days after, 7 days after, 14 days after, etc.) of the aligner to the teeth. Thus, any of the methods described herein may be used to monitor tooth movement during an orthodontic treatment.

The methods described herein may also or alternatively be used to examine the connection of an orthodontic appliance, such as an aligner, to the teeth. For example, the interaction between the dental appliance and one or more attachments coupled to the patient's teeth may be examined using the OCT methods and systems described herein.

In some variations, the methods an apparatuses described herein may be used and/or useful to visualize collisions between teeth during an orthodontic treatment plan directly, which may also allow adjusting of the treatment plan.

The methods and apparatuses described herein may also be used to detect structures within the oral cavity (e.g., teeth, gingiva and/or palate), as described above. For example, the methods and apparatuses described herein may be used for sub-gingival scanning, allowing imaging of sub-gingival regions of the teeth.

For example, in some variations a method of monitoring a dental treatment (including monitoring tooth movement, collisions, etc.) may include: (1) scanning a 'pre-scan' of the patient's teeth using OCT without any appliance applied to the teeth; (2) attaching the appliance to the patient's teeth (e.g., snapping it on to the patient's teeth); (3) scanning the patient's teeth and appliance when the appliance is worn on the teeth; and (4) analyzing the data, which may include determining the points of contact with the teeth and the appliance(s), between any attachments on the teeth and the appliance(s), between the tooth and an attachment, tooth movements, etc. The analysis may also include adjusting the patient's treatment plan based on analyzed data. For example, in some variations the scan may include the attachment-tooth interface to evaluate bonding of attachment; voids at the interface between the tooth and the attachment may indicate a potential source of attachment falling. In some variations, the scan may also be used to examine the status of the soft tissue. For example, an analysis of the soft tissue my reveal cancerous soft tissue.

OCT System

The methods and apparatuses described herein may also be configured as intraoral scanners for visualizing depth under the outer surfaces of the oral cavity and/or any appliances. Intraoral depth scanning using optical coherence tomography may allow for the visualization of objects outside of the teeth (e.g., aligners) and within the tooth (e.g., caries, cracks, developmental defects of enamel).

For example, OCT may be integrated in line with the optics or fixed on the side of an existing intraoral scanner, so that the field of view from the OCT may be known to be at a fixed location relative to the scanner head. In some variations the OCT may be combined with surface scanning (e.g., using visual light). In addition to surface scanning, the OCT apparatus may take a series of OCT 2D scans (B scans) that may be captured at high frame rates. Given the known fixed position between the OCT 2D scan relative to the surface scan, the OCT data can be merged to form a model (including a volumetric model) of the patient's oral cavity, which may include the teeth alone and/or the teeth and an appliance.

In some variations, the calculations (OCT alone or OCT and surface scanning) may be performed in real time with parallel processing, which would make it suitable for intraoral use with minimal movement artifacts. At sufficiently high scanning rates, the scans may be stitched together to image a larger field of view than individual scans, in real time. Thus, the method and apparatuses described herein may be used to produce depth information beyond a simple surface scan, in real time which makes it appropriate for intraoral patient use.

To date, existing OCT systems have proven somewhat slow in scanning. The methods and apparatuses described herein may be used to take full tomographic scans that are faster than traditional "slow" scanning by using swept source OCT that typically scans a small area, such as a 5 mm×5 mm lateral area. For example, a single tomographic 3D scan may be constructed of a series of independent 1 dimensional scans (in the depth dimension) that are rastered in the remaining two dimensions. It is possible to detect relevant surfaces (e.g., tooth surfaces, aligner surfaces, etc.) from a single scan, enabling rapid parallel processing.

Figure 6A:
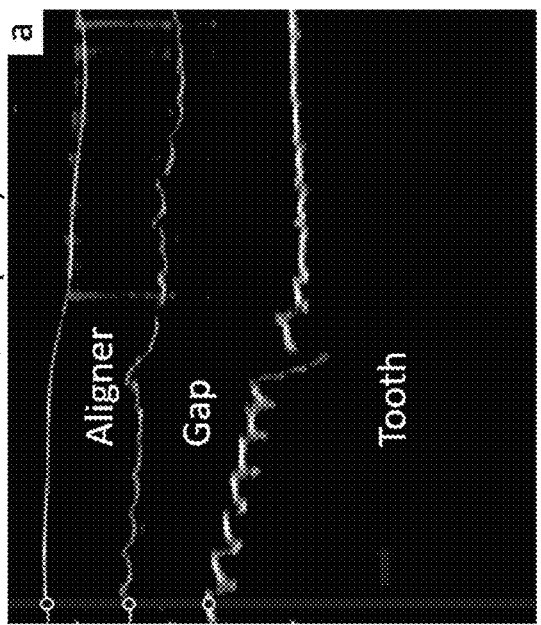
FIGS. 6A-6C illustrate one example of image processing through a single slice (e.g., z-section) of scan data for an OCT system (voxel system).
Figure 6B:
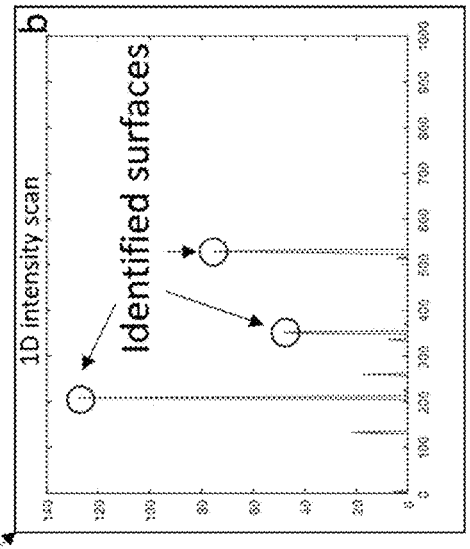
Figure 6C:
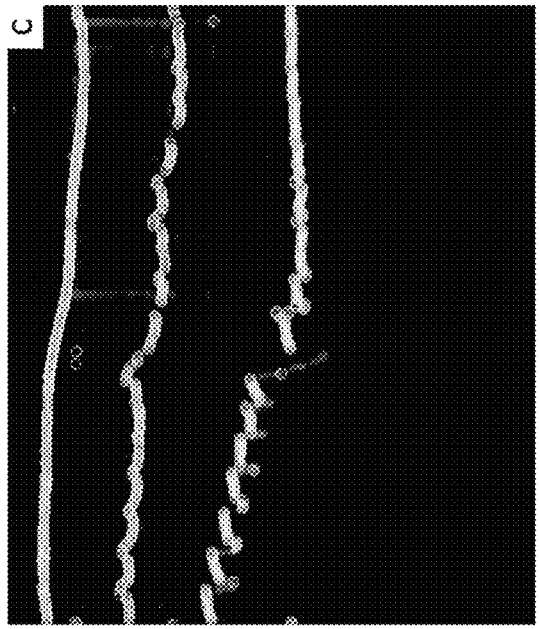

For example, FIGS. 6A-6C illustrates one example of an OCT 2D image processing. In FIG. 6A, a raw OCT 2D slice shows both aligner surfaces (top and middle surfaces) and the underlying tooth surface (bottom surface). The vertical line on the left 601 represents the location of the 1D line for the image shown in FIG. 6B. Peaks in the 1D line can be identified as surfaces and extracted, as shown in FIG. 6C. In FIG. 6C, the result of the 1D line surface extraction across the second dimension are shown, showing different extracted surfaces.

As mentioned before, there may be an appreciable time lag OCT scanning of larger regions (e.g., in some examples, it may take 5 seconds or longer to capture an entire 3D volume). This delay typically makes real-time scanning challenging. However, described herein are techniques that may allow faster imaging even while using such typically slower scanners (e.g., scanning with the same parameters). For example, a single 2D scan can be captured repeatedly at high speeds (about 50 frames a second) which may be appropriate for real time scanning. Thus, a high-speed 2D OCT scanner can be integrated into a traditional intraoral scanner in order to augment its surface measurements. For example, wavelengths can be integrated directly into the optics of a scanner or be fixed to the scanner at an offset; either way, the location of the field of view with respect to the scanner is known.

A "template" surface may be generated from a traditional (e.g., non-OCT, surface) scanner. Augmented information may be collected from OCT 2D scans which may be processed in real time and superimposed on the template surface. Any augmented information produced in this manner could include, but is not limited to, aligner/tooth gap, aligner thickness, and presence of enamel mineral changes (either by developmental defects or dental caries).

Figure 7:
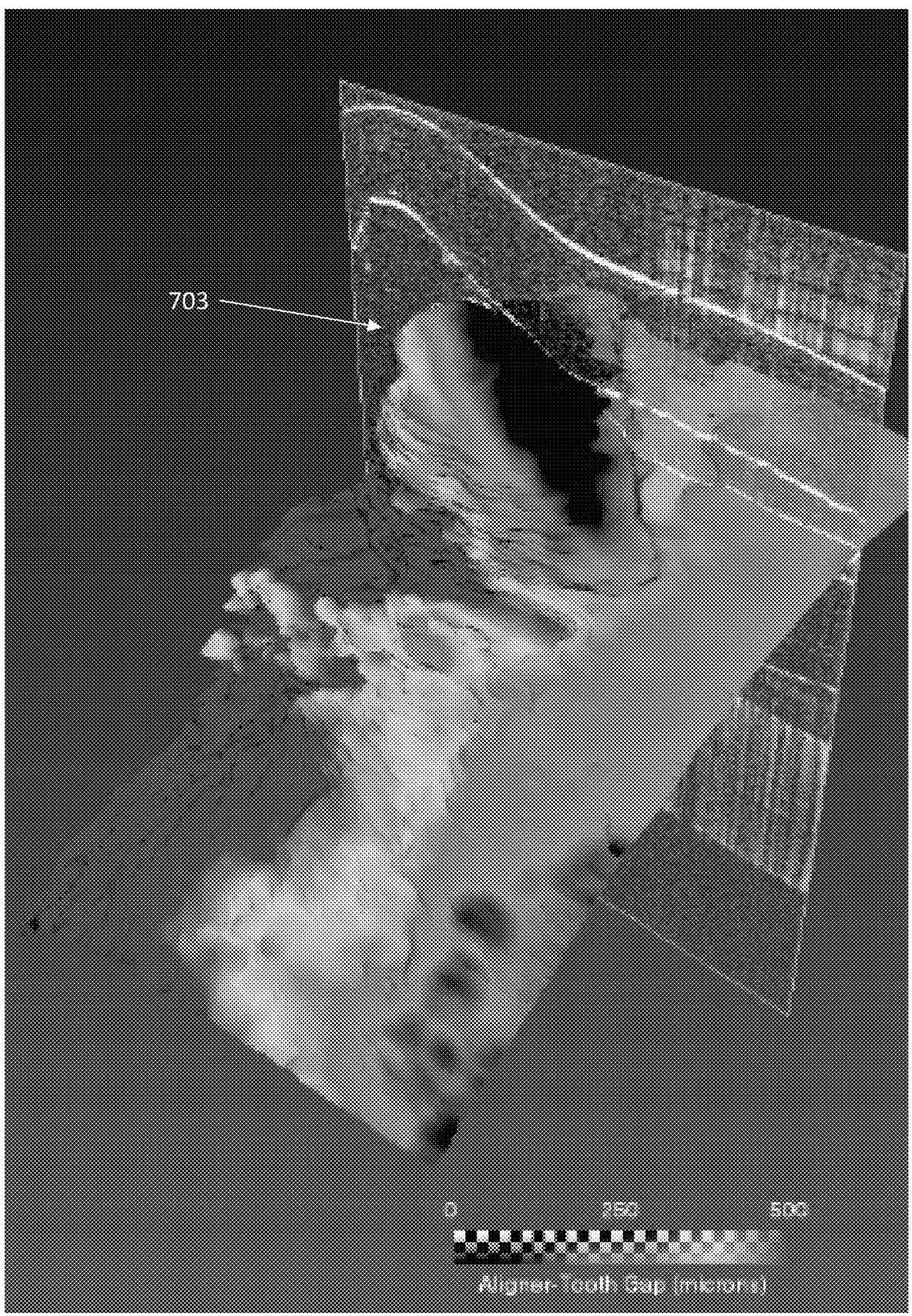
FIG. 7 is a heat map of a single surface isolated from the voxel information in the OCT data. This surface is an aligner inner surface.

For example, FIG. 7 shows an example of a tooth with attachment bonded to the tooth for interacting with an aligner. The heat map (which may be shown in color), may be superimposed and may represent a gap between the tooth (or an attachment on the tooth) and the aligner. In FIG. 7, the heat map shows that the attachment is engaged on the active surface of the aligner, which is very close to the tooth, on at least one side of the attachment 703. In this example, the 2D section shows registered OCT data.

OCT Scanning for Appliance Design and Verification

Also described herein are systems for usage of OCT scanner for orthodontic aligner design validation and verification. This example includes the methods and apparatuses, including software. For example, described herein are OCT dental scanners (including, but not limited to intraoral scanners) that may be configured to collect, process, display and/or analyze OCT images of a patient's teeth, model teeth, teeth of aligner testing apparatus, and/or a dental appliance. The scanner results may include 3D matrix of light intensity values, and extract inner and outer surfaces of aligner, as well as teeth surface, out of this data. Given that individual scan areas may be relatively small (e.g., ~5 mm size 3D box), multiple scans may be made and the individual scans stitched together. As scanner position may be unknown, stitching has to be performed automatically by the software and may be done in a variety of ways, including using feature detection and matching.

The OCT scanning technology may be used in orthodontic aligner design. A system may include: (1) an OCT scanner; (2) a scan aligner (e.g., software, firmware and/or hardware) for aligner and teeth surfaces extraction. These two components may be separate or may be combined into a single apparatus.

Using surfaces extracted, areas of direct contact between aligner and teeth may be identified and this information may be used for aligner's design validation/verification, as well as for more accurate mechanical stress analysis of the aligner, as mentioned above. This provides accurate detection of contact areas between teeth and aligner, with the precision of OCT scanner, which is typically in the micron range. The system may allow validation of dental apparatus (e.g., aligner) design as well as dynamic simulation of mechanical stress with higher precision. OCT scanner technology may provide intensity profile with fine resolution (e.g., with a grid step size of about 5-8 um) and of acceptable quality. By scanning a 3D region of interest, which may include a portion of an appliance and/or teeth, and obtaining volumetric intensity profile, this data can then be used by to analyze intensity volumetric data, extract inner and outer surfaces of aligner, as well as teeth surface. It may also be used to identify areas of contact between teeth and inner aligner surfaces. Alternatively or additionally, it may be used to output extracted 3D mesh data in some established formats, such as STL and PLY. This data can then be used for design validation of an appliance, as well as by mechanical stress simulation tools to simulate alignment dynamic process helping to apply forces more precisely and hence achieve better quality of results of simulation. Any of this information may also be used to improve the design of a series of aligners, for example, as feedback for the sequencing, timing or duration of tooth movement.

The systems and methods described herein may address some of the challenges of OCT scanning. For example, typical scanner results may contain a lot of artifacts including, but not limited to: "salt and pepper" noise; vertical and horizontal stripes; and/or missing parts of surfaces' profiles. FIG. 8 shows an example of a raw OCT scan through a dental appliance worn on a patient's teeth, showing such artifacts. For example, salt and pepper noise 803, missing regions 805 and horizontal strip artifacts 807. Such artifacts should be removed before surface extraction, in order to achieve acceptable level of precision of extraction. To enable this, multiple signal processing and filtering techniques may be used, including implementing a median filter, a rotating kernel filter and/or other filters, including novel filtering mechanisms developed using heuristics specific to OCT images made of aligner and teeth described herein (which may be referred to herein as "dental filtering").

The material forming a dental appliance (e.g., aligner) may have a refractive index that is different from air. Thus, special procedures may be implemented to obtain geometrical data out of optical path length data.

The scanned region (plane or volume) is generally small (e.g., 5 mm on each side) compared to the size of the whole jaw. To scan an object larger than the field of view of the OCT scanner, images can be recorded from multiple positions and orientations and then stitched together to form a single full image of the object(s). As scanner position may be not known, automatic stitching and calculation of mutual positions and orientations of single scans obtained may be used. If the individual images are small relative to the features of the object, accurate stitching may be difficult. Additionally, if many images are needed to cover the object, it may become computationally expensive to determine which images are adjacent to each other. By attaching a tracker to the OCT probe, one can record the position and orientation of the probe relative to a reference frame for each image. This may simplify the task of stitching images, since identifying the adjacent images from this information is easy and because the algorithm will have a good starting point for the final match. A tracker may track positon of the OCT probe based on magnetic fields; alternatively or additionally, other tracking technologies could be used, e.g. ultrasonics, stereovision of optical targets, integration of accelerometer, gyroscope, and gravity sensor, magnetometer, etc. To avoid issues caused by patient movements, the reference for the tracker (e.g., the transmitter) can be mounted on a fixture anchored to the teeth or head. Examples of commercial trackers that may be adapted for use in the systems described herein may include the Polhemus or Ascension Technology trackers.

Also described herein are methods and apparatuses for surface extraction from 3D volumetric intensity profile that allow precise and fast reconstruction of tooth and/or appliance surfaces. Other surface reconstruction methods may, given a set of 2D images taken from the different angles of view, build 3D volumetric data; the methods and apparatuses described herein may instead extract 3D surfaces out of given 3D volumetric data, since the OCT scanners described herein output volumetric data (e.g., voxel maps) for relatively small 3D region (e.g., ~5 $mm^3$ cubes). To build more or less complete images, multiple scans may be taken for different 3D regions. However, this may result in unknown mutual positions of those regions.

In operation, these methods may read in a voxel map for multiple scans made by the apparatus, stitch them all together, extract surfaces, including (but not limited to): the aligner's outer surface; the aligner's inner surface; and the teeth surface. The methods may also identify areas of contacts between inner aligner surface and teeth and may match extracted data (e.g., with ADF). These methods may be used to obtain contact areas and deformed shape of a dental appliance directly, without requiring a time-consuming simulation.

Figure 9A:
FIG. 9A is an example showing three extracted surfaces (tooth, aligner inner, aligner outer) for a single scan of an OCT scanning device (e.g., a 5×5×5 mm region).
Figure 9C:
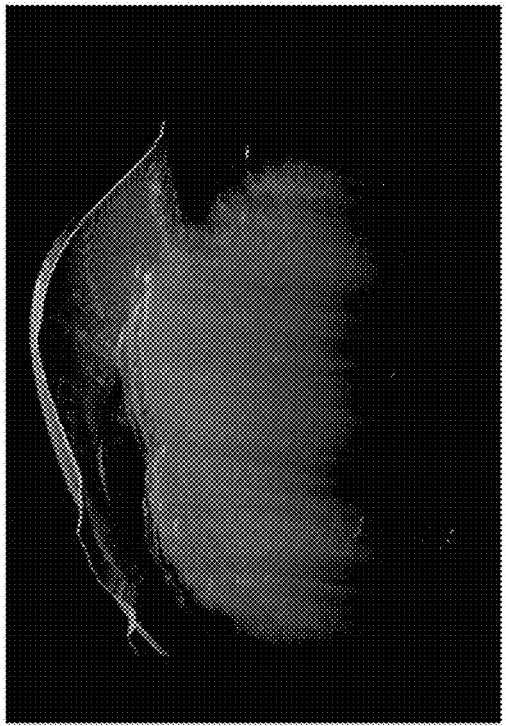
FIGS. 9B and 9C show two views from different angles of superposition of both extracted surfaces and rendered raw OCT data.
Figure 9B:
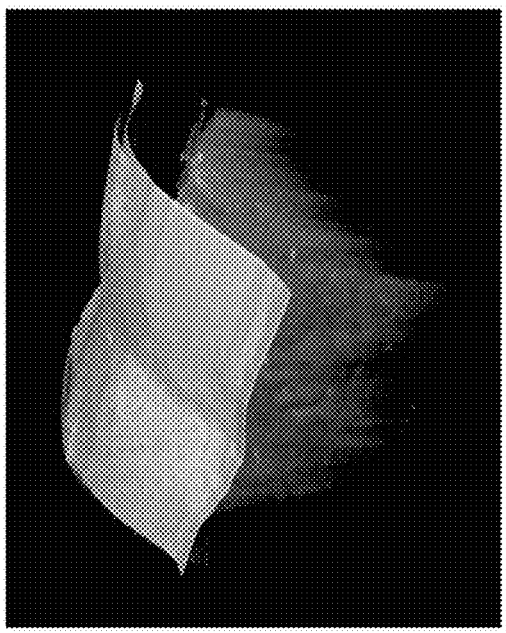

The interpretation of OCT data may be performed in real-time and/or after scanning, and may be done as part of a dental appliance (e.g., aligner) treatment planning method. The analyzed data may be stored as a single database (or file) or as commonly-referenced data (e.g., files). For example, the data received from the OCT scanner (e.g., an intraoral OCT scanner) may be received as a series of voxel maps that are stitched together, and the final combined voxel map may be processed to determine surfaces, as mentioned above, including outer appliance surface, inner appliance surface, and teeth surface. In some variations the contact surface(s) between these surfaces may be identified. For example, the multiple file for each type may be used, such as: outer aligner surface, inner aligner surface, teeth surface(s), and/or contact area. In addition, one or more files with all or some of these surfaces combined may be included (e.g., file with all surfaces together painted with different colors). FIGS. 9A-9C illustrate one example of this. FIG. 9A shows the outer aligner surface 903, the inner aligner surface 905, and the outer surface of the teeth 907, showing a region of contact 909. FIGS. 9B and 9C show views of a region of the teeth and aligner showing both the outer and inner aligner surfaces as well as some detail on inner structures of the teeth.

Figure 10:
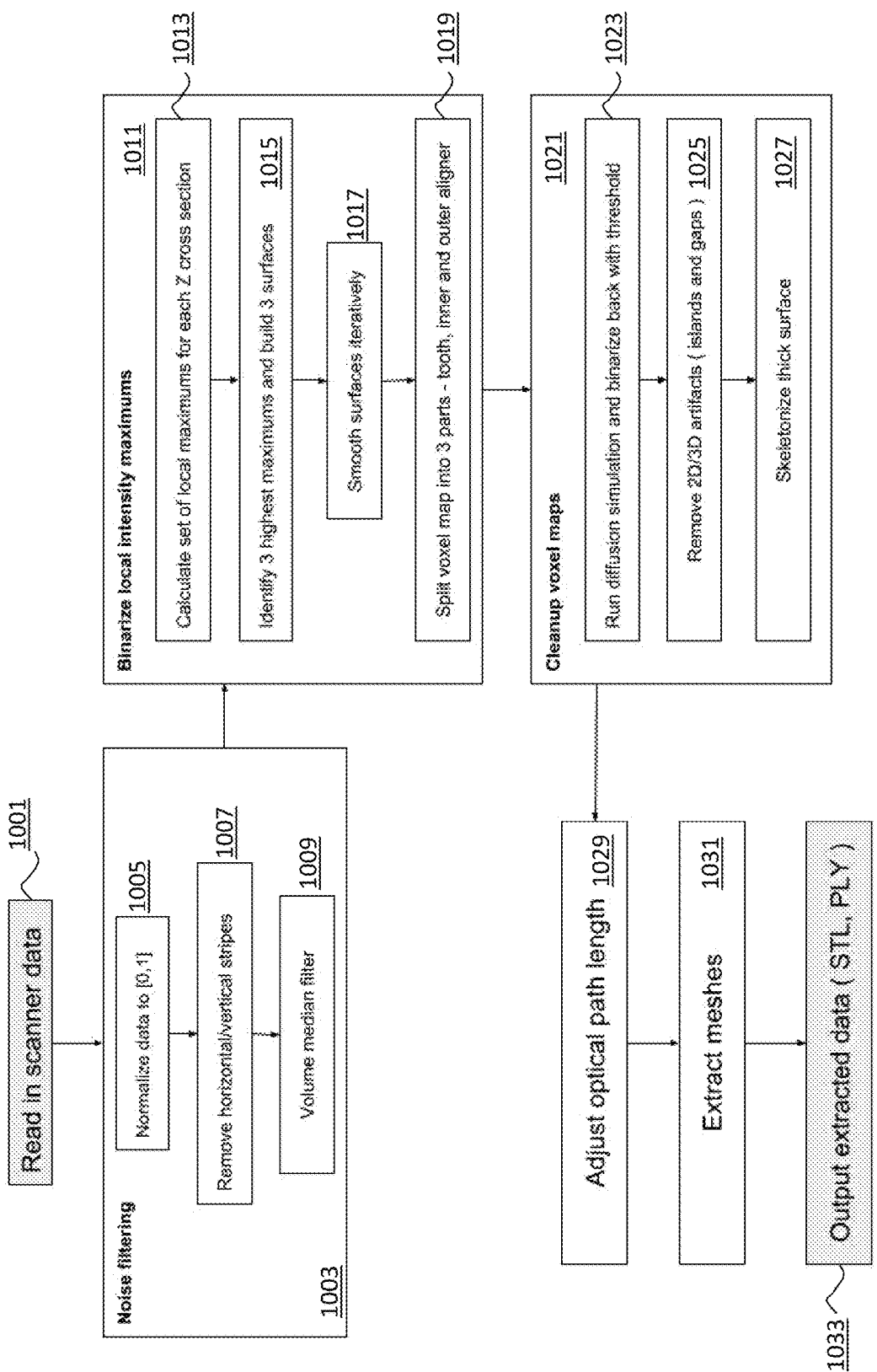
FIG. 10 illustrates one example of a workflow for processing single scan raw OCT data of a patient's teeth and/or aligner, including operation of a voxel mapper (including a noise filter, parser, cleaner and finisher) for performing the workflow.

FIG. 10 illustrates an example of a workflow (e.g., method) for OCT imaging and processing. In some variations, the scanning may occur first using an OCT scanner. The OCT scanning may occur as described above (e.g., using an OCT scanner, such as an intraoral OCT scanner), which may scan in regions (e.g., 5 mm×5 mm×5 mm volumes) as voxel information. In FIG. 10, each individual volume (sub-volume) may be prepared before or after stitching. For example, each volume/sub-volume may be passed from the scanner ("read scanner data") 1001 to a noise filter 1003. The noise filer may filter the noise from the voxel information by, for example, normalizing the data 1005, removing horizontal and/or vertical stripes 1007, and/or applying a median filter (volume median filter) 1009. The initially filtered voxel information (data) may then be passed to a parser 1011 to binarize local intensity maximums 1009. The parser may calculate a set of local maximum for each Z cross-section 1013, identify some number (e.g., 2, 3, 4, 5, etc.) of highest maximums and build corresponding surfaces (e.g., 3 surfaces). These surfaces may then be smoothed 1017, e.g., by iterative smoothing, and the voxel map may be split into multiple parts (e.g., 3 parts). In some variations the parser may be configured specifically to the dental device, such as an aligner, worn on a subject's teeth, and may be configure to 'expect' this configuration. For example, the parser may be configured to specifically identify three surfaces corresponding to the inner aligner surface, outer aligner surface and tooth (e.g., 3 parts). In some variations the parser may confirm that the expected structures are present by, for example, verifying that the local maximums are within an expected range.

Once the surfaces have been identified, smoothed and separated into voxel maps, the voxel maps may be cleaned up using a cleaner 1021. The cleaner may run a diffusion simulation first and then binarize back with a threshold 1023, and may remove two-dimensional (2D) and/or three-dimensional (3D) artifacts such as islands and/or gaps 1025. The cleaner may also skeletonize the thick surface(s) in the voxel map 1027. Finally, a finisher may adjust the optical path length 1029, and/or extract meshes 1031, and the extracted data may be output in an appropriate format for storage, display and/or manipulation 1033 (e.g., as STL or PLY files).

The noise filter, parser, cleaner and finisher may be circuitry, and may include one or more processors, which may be configured to execute programs (e.g., code) to manipulate the data. The noise filter, parser, cleaner and finisher may be collectively referred to as a voxel mapper.

Figure 11:
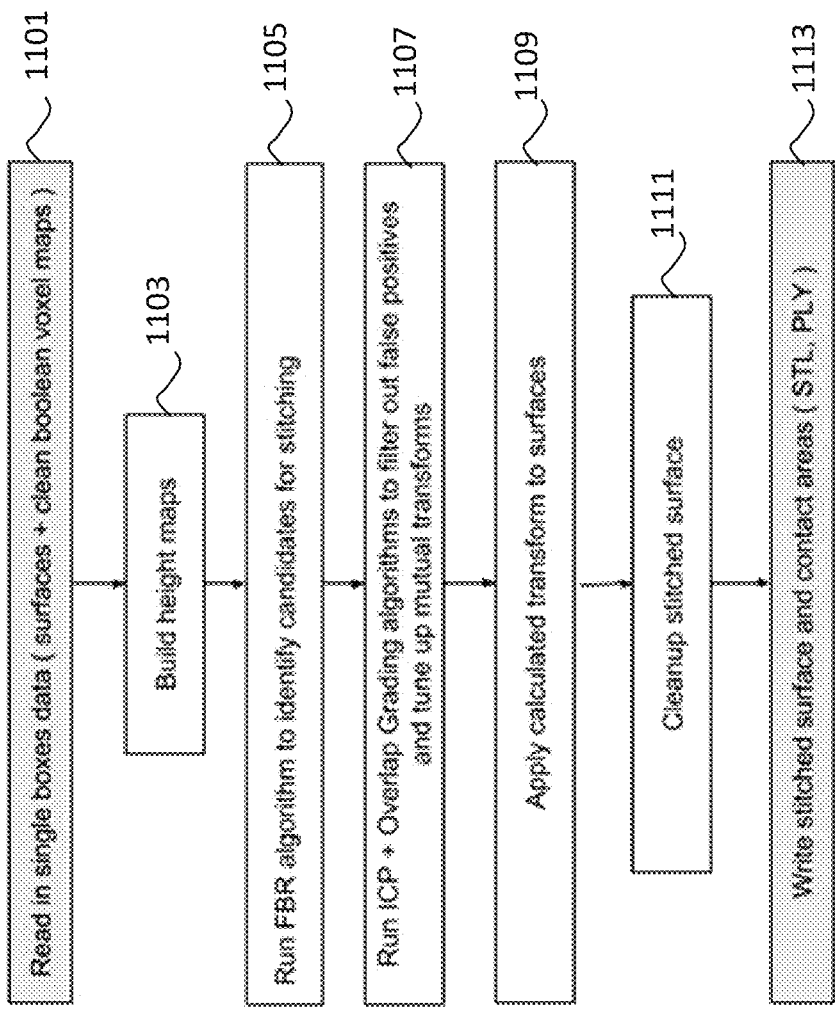
FIG. 11 illustrates one example of a workflow for stitching multiple OCT voxel datasets together, including operation of a stitcher for performing the workflow.

As mentioned, the voxel map(s) may be stitched together either before and/or after processing by the voxel mapper. FIG. 11 illustrates one example of a workflow for stitching multiple voxel maps together; in FIG. 11, the voxel maps are stitched together after processing by the voxel mapper. For example, in FIG. 11, a voxel stitcher (or stitcher) receives the plurality of voxel maps that have been processed by the voxel mapper 1101, which has identified the surfaces and cleaned the voxel maps. The stitcher may then build height maps 1103, and identify candidates for stitching 1105. In some variations the stitcher may perform one or more algorithms looking for overlapping regions to identify these candidates. For example, feature base registration (FBR) may be used. After collecting candidates (mutual transforms) by FBR, they may be tuned by applying iterative closest point (ICP) procedure to minimize the discrepancy in overlap areas. For example, overlap grading may be used to find best candidates among all suggestions made by FBR. In addition, candidates appeared to be false positives may be filtered out 1107. Surfaces in the data may then be combined by applying a calculated transform 1109. Stitched surfaces may then be cleaned up in overlap areas based on the transforms calculated; as part of this process, mesh artifacts may be cleaned up, including removing/patching holes, self-intersections, etc. Thus, once combined, the stitched surfaces may be cleaned up 1111 and the combined surfaces prepared for output (e.g., as files such as STL or PLY files) 1113; the 3D surfaces may then be stored, displayed and/or processed further.

Figures 12A, 12B:
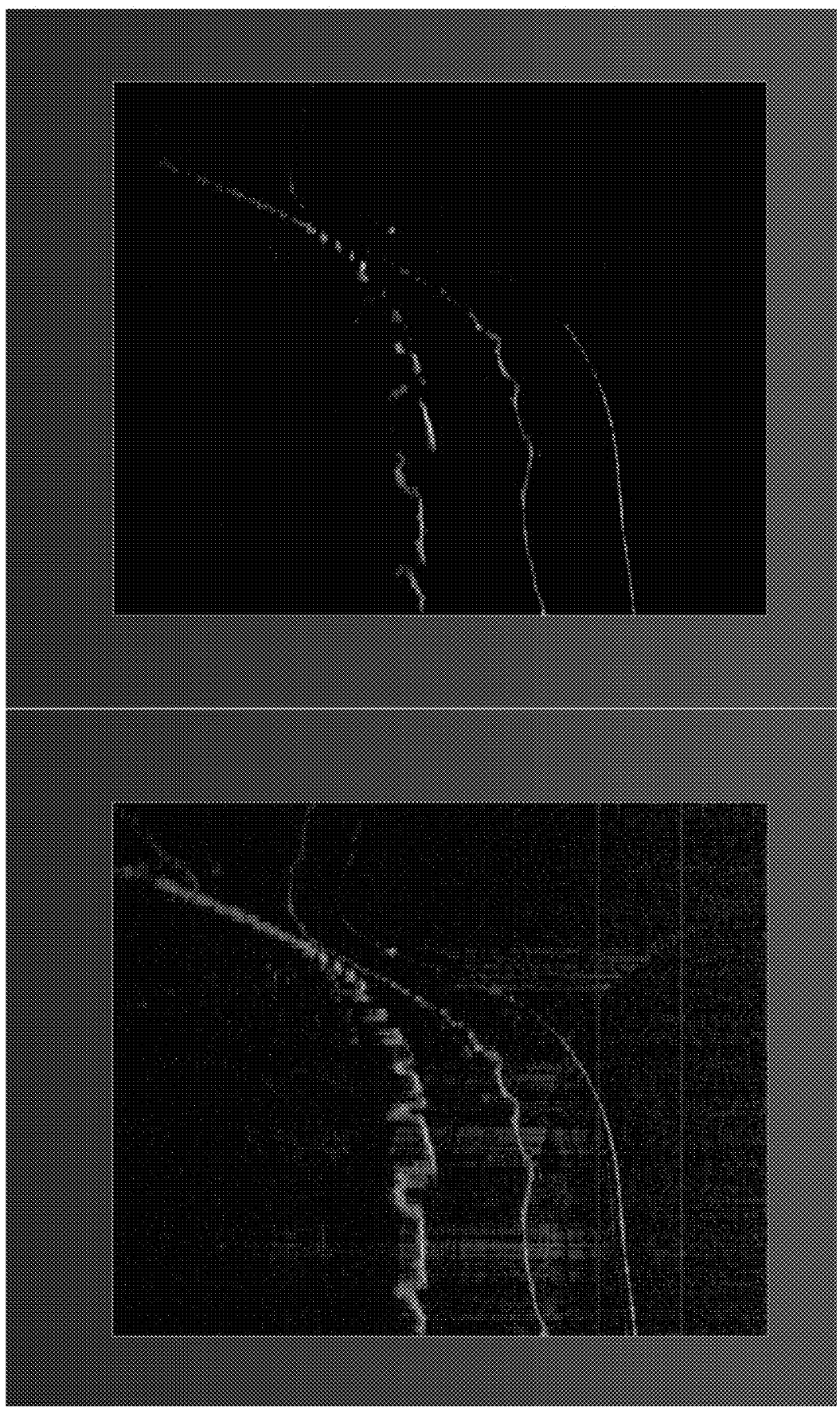
FIGS. 12A-12B illustrate the operation of a noise filter of a voxel mapper for processing raw OCT data.
Figures 13A, 13B:
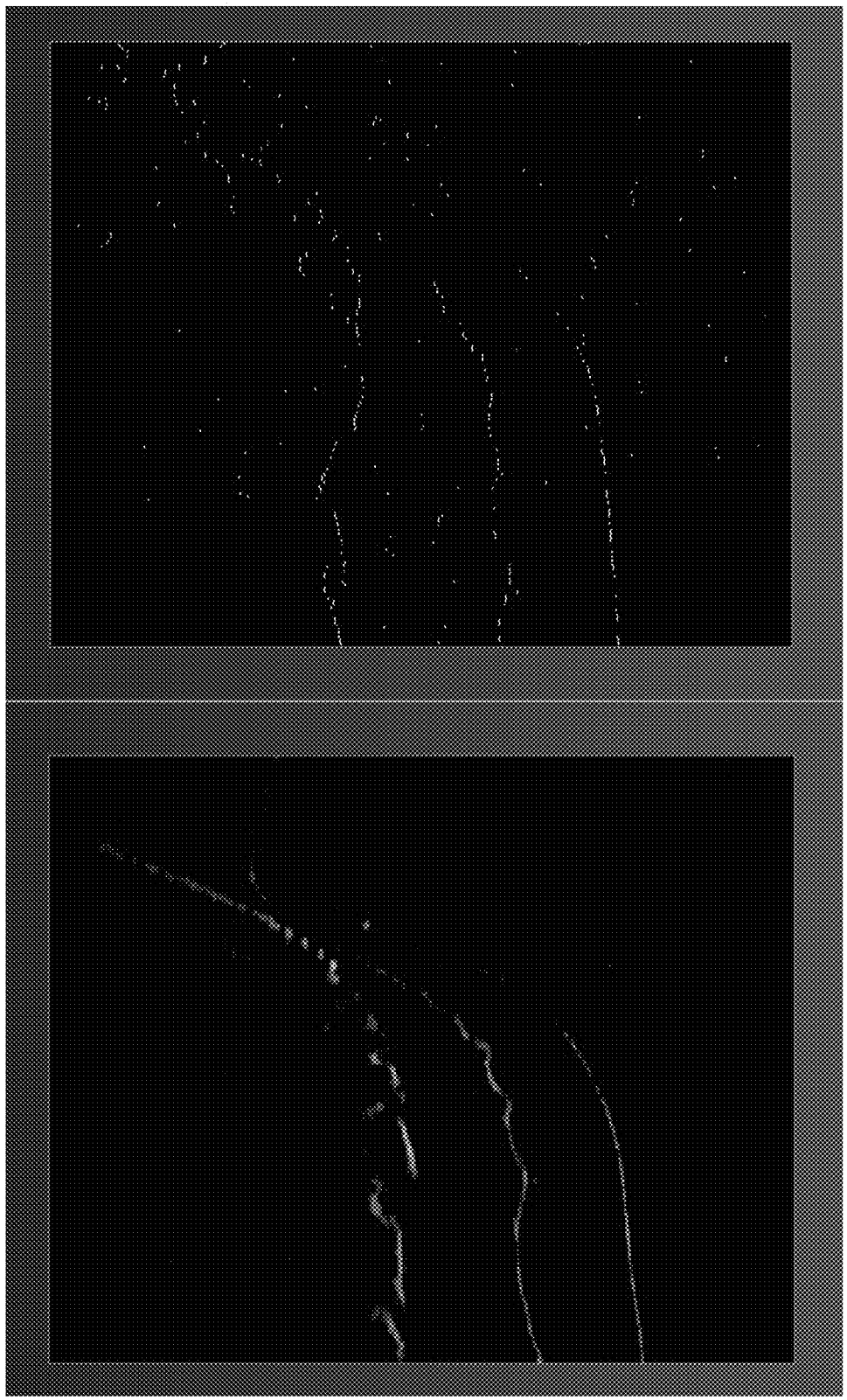
FIGS. 13A-13B illustrate operation of a parser of a voxel mapper for identification of local intensity maximums of OCT data after noise filter.
Figures 16A, 16B:
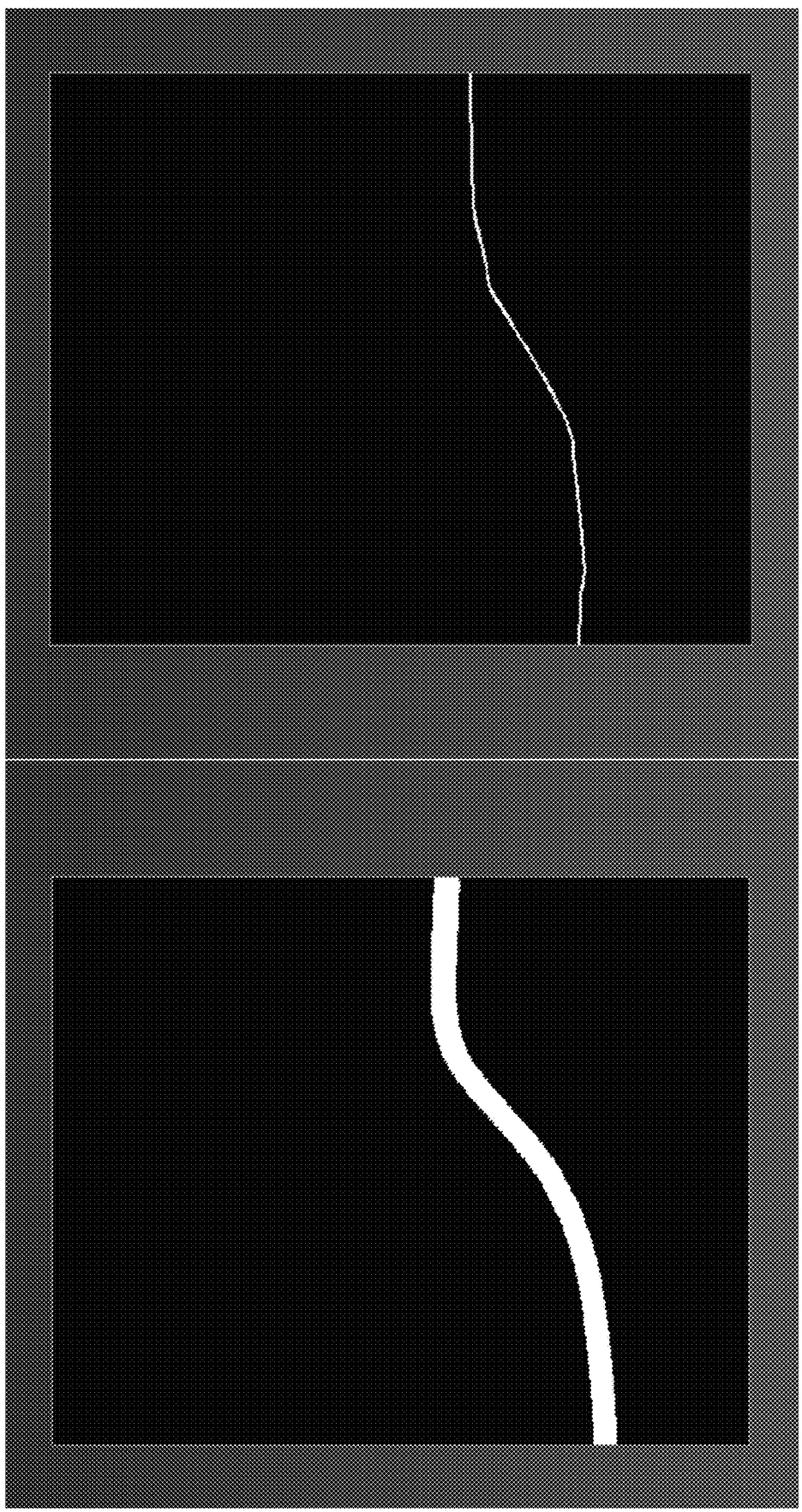
FIGS. 16A-16B illustrate further cleaning the isolated surface from the OCT volume shown in FIG. 15B by skeletonizing the surface (FIG. 16B).
Figure 18:
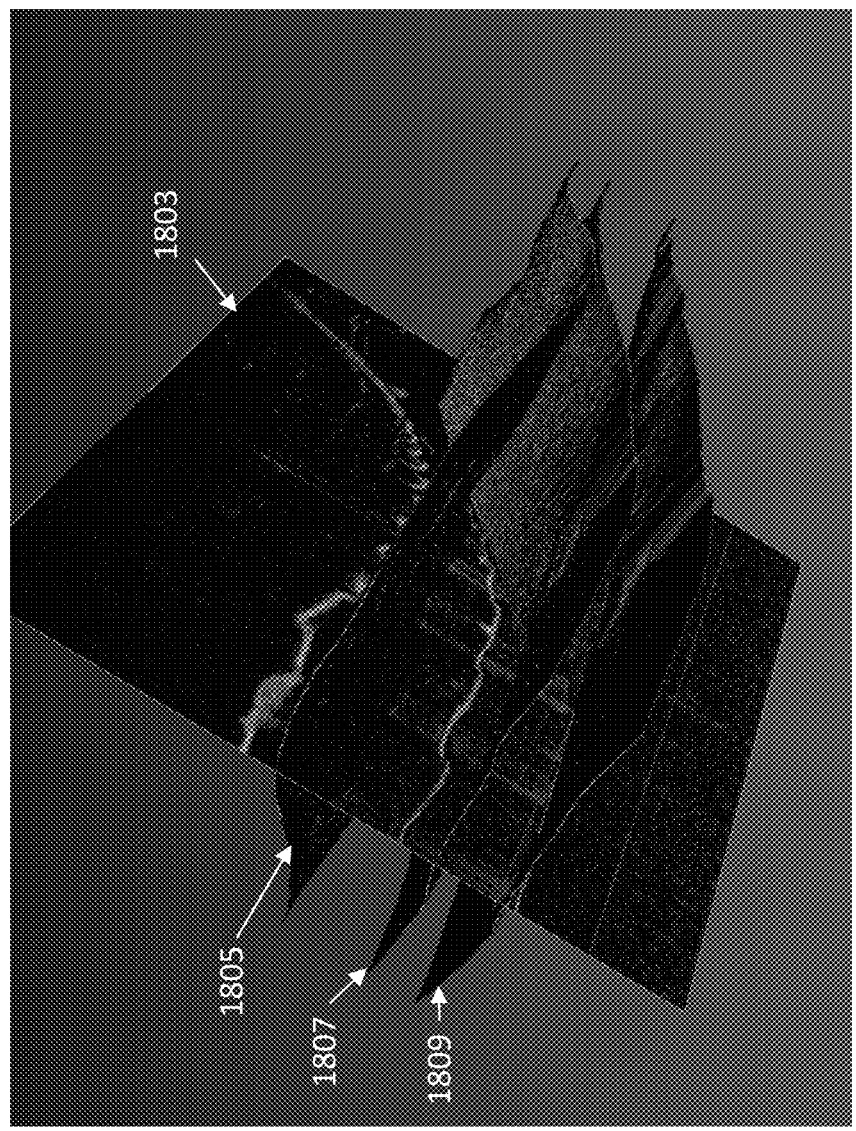
FIG. 18 illustrates the three extracted surfaces from the exemplary OCT volume processed as described and illustrated in FIGS. 12A-17B, superimposed with cross-section of raw OCT data.

FIGS. 12A-18 illustrate an example of the operation of a voxel mapper. For example, an OCT volume from a scanner ("read scanner data") may be filtered by a noise filter, as shown in FIGS. 12A-12B. In FIG. 12A, a section through the unfiltered volume is shown. The noise filter filters the noise (e.g., vertical and horizontal stripes, salt-and-pepper noise) from the voxel information and normalizes the data to [0,1] range, to produce a cleaned volume, as shown by a section through the volume in FIG. 12B. The filtered voxel information (data) may then be passed to a parser, shown in FIGS. 13A-13B to collect the local intensity maximums. FIG. 13A shows the filtered view prior to parsing, FIG. 13B shows a view of the volume after parsing. The parser calculates a set of local maximums for each Z cross-section (a single cross-section is shown in FIGS. 13A-13B), in which three surfaces were identified and smoothed, as shown in FIGS. 14A-14D. FIG. 14A is the same as FIG. 13B. FIG. 14B isolates a first surface (e.g., aligner outer surface), FIG. 14C shows the isolation of a second surface (e.g., aligner inner surface) and FIG. 14D shows the isolation of a third surface (e.g., tooth). These surfaces may then be cleaned (using the cleaner), as shown in FIGS. 15A-15B, for example, using a diffusion algorithm. FIG. 15A shows on of the isolated surfaces (the first surface similar to that shown in FIG. 14B) and FIG. 15B shows the same surface after cleaning by a diffusion algorithm has been used. The cleaning may result in a thickening of the surface, which the cleaner may correct by skeletonizing, as shown in the example of FIGS. 16A-16B. FIG. 16A shows a section through one of the three isolated surfaces (e.g., the surface shown in FIG. 15B) after cleaning, while FIG. 16B shows the same surface following skeletonizing. Any two-dimensional (2D) and/or three-dimensional (3D) artifacts, such as islands and/or gaps, may be repaired by the method. The voxel map(s) may then be processed by the finisher, which may adjust the optical path length, as shown in FIGS. 17A-17B. From these processed voxel maps, the complete surfaces may be extracted, by building height map based on the cleaned voxel map and applying direct triangulation to the given height map. FIG. 18 illustrates one example showing the three extracted surfaces 1805, 1807, 1809 (also showing a representative single xz-section 1803, corresponding to the section shown in FIGS. 12A-17B).

Monitoring Palatal Expansion

The methods and apparatuses described herein may also be used to image the palatal suture, including internal portions of the palate, without ionizing radiation. The palatal suture is not commonly monitored in dental treatments, as it may be difficult to image, particularly internal structures. The methods and apparatuses described herein may be used to image both the outer surface and regions within the palate. For example, the methods and apparatuses described herein may be used to image the palatal suture and may therefore be used to monitor the progress of therapies such as palatal expansion.

Figure 4B:
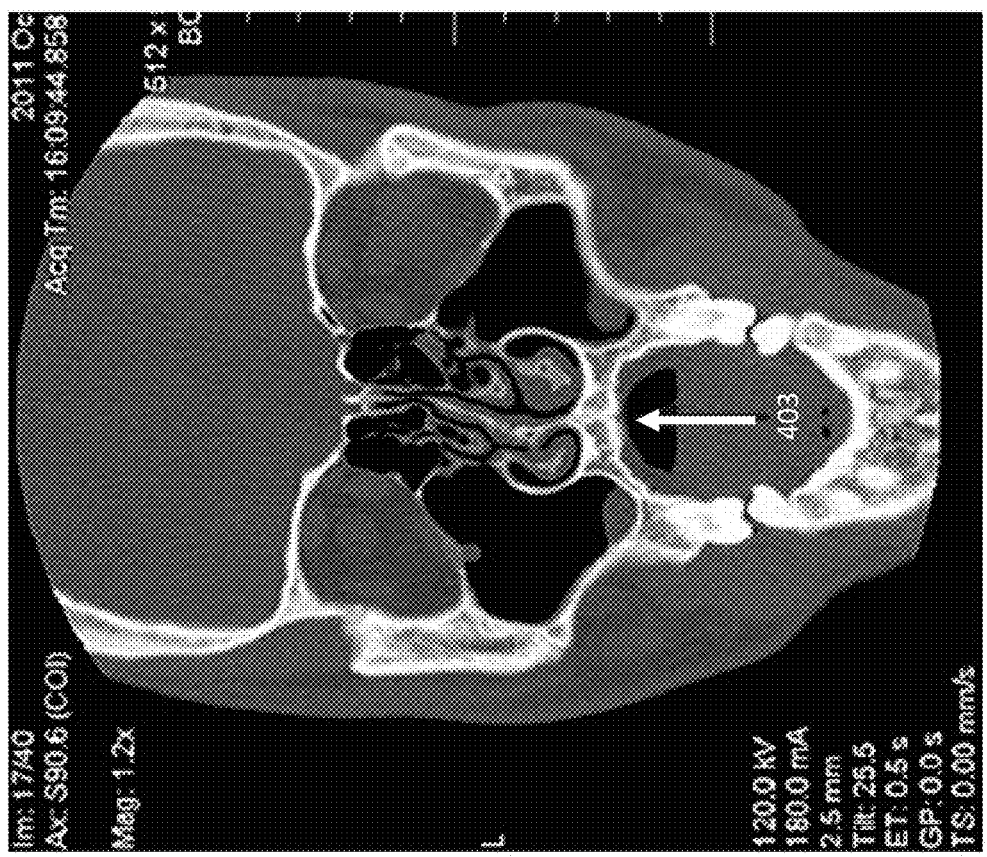
FIGS. 4A and 4B illustrate examples of palatal anatomy that may be visualized using the methods and apparatuses described herein.
Figure 4A:
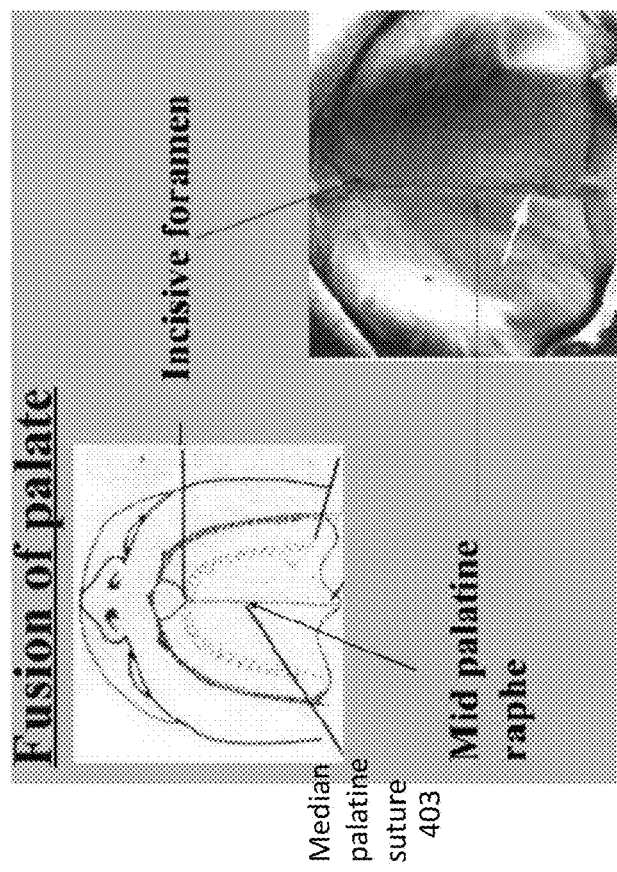

As shown in FIGS. 4A and 4B, the mucosa tissue at the mid palatine raphe is very thin and therefore an intraoral scanner scanning in the near-IR wavelength (e.g., 850 nm, 880 nm, 900 nm, 950 nm, etc.) may be used to determine the palatal suture. This technique may allow palatal expansion (e.g., by a palatal expander) to be monitored during the treatment without need to take CT scans. In FIG. 4A, the midline of the palatal region is the palatal suture (e.g., mid-palatine raphe). As further shown in FIG. 4B, the thickness of palate mucosa at the mid palatine raphe is relatively thin, and may be readily viewed using the methods and apparatuses described herein.

Figure 5:
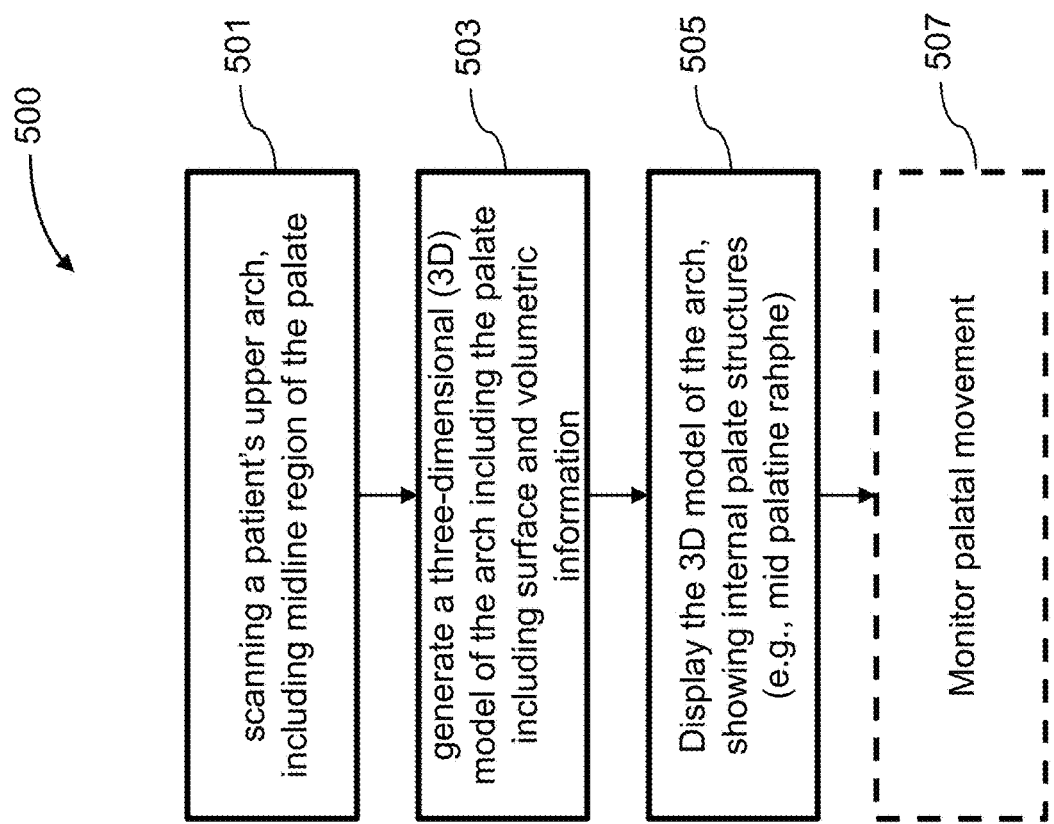
FIG. 5 is a diagram illustrating a method including imaging a patient's palate as described herein.

For example, FIG. 5 illustrates one method for monitoring the palatal suture 500. In this method, an intraoral scanner that is capable of scanning both surface scans and penetrative (e.g., near-IR scanning, and in particular OCT scanning) may be used. In this example, the scanner is used to scan a patient's upper arch, including midline region of the palate 501. This scan may be an OCT scan, as described above, or any other penetrative scan. A surface scan may be taken at the same time. The upper arch, including one or more tooth or teeth may be scanned, in addition to the palatal region.

The scans of the upper arch may be used to generate a three-dimensional (3D) model of the arch, including the palate including surface and volumetric information 503 within the arch (e.g., the suture region). For example, the OCT images may be used to generate a 3D volumetric model of the dental arch. The use of the OCT images to reconstruct a 3D model (e.g., a volumetric model) may be an optional step. The 3D model of the arch may be displayed, and/or images (OCT images) of the dental arch, including the suture region, may be displayed, showing internal palate structures (e.g., mid palatine rahphe) 505. A time series of such images or models may be made over time, allowing the dental practitioner to monitor the progress of treatment (e.g., palatal expansion treatment, dental alignment treatment, etc.) 507.

In some variations, the software may automatically determine an expansion rate of the suture. For example, the software may include an automated agent to detect certain reference points on the suture line and determine the expansion rate over time. The reference points may be based on existing anatomical landmarks or distinctive regions or they may be added/artificial (e.g., temporary anchorage devices, or TADs, etc.).

In any of these variations, partial scans may be taken and connected (e.g., "stitched") together.

Attachment Verification

Figure 19A:
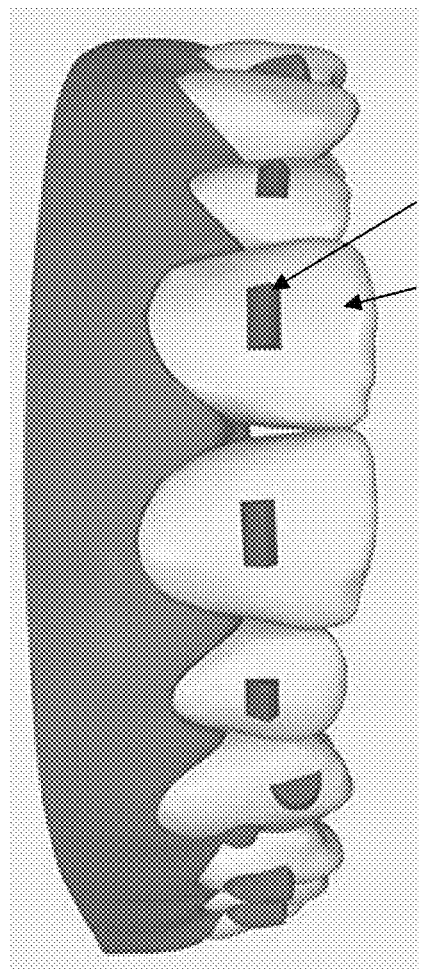
FIG. 19A illustrates one example of a set of teeth having attachments bonded on the tooth to engage with an aligner (not shown in FIG. 19A). Attachments may be any appropriate size and shape. The OCT methods and apparatuses described herein may be used to examine, via OCT scanning, the connection between the attachments and the teeth.
Figure 19B:
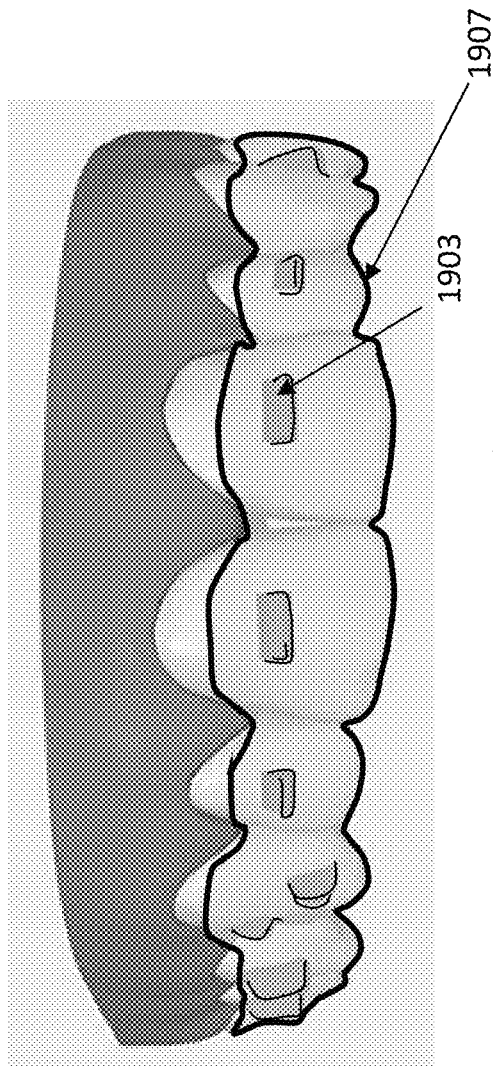
FIG. 19B illustrates the set of teeth with attachments shown in FIG. 19A with an aligner coupled to the teeth and attachments. The OCT methods and apparatuses described herein may be used to examine, via OCT scanning, the connection between the attachments and the aligner.

As mentioned, also described herein are methods and apparatuses for scanning (e.g., using OCT) at high resolution either the connection between an attachment 1903 and a tooth 1905 (see, e.g., FIG. 19A) or the contact region(s) between an aligner 1907 and the attachment 1903 on a tooth (see, e.g., FIG. 19B).

Typically, the initial attachment placement on the teeth by the dental practitioner (e.g., dentist, orthodontist, dental technician, etc.) is time consuming, and it may be difficult to verify proper placement of attachment. In addition, misplaced attachments can lead to an unintended orthodontic force system. The methods and apparatuses described herein may allow for a dental practitioner to scan and adjust attachments (e.g., clear aligner attachments). These methods and apparatuses may also verification of correct attachment placement, which may include a check to see if attachments appear fully filled (i.e., no voids) and if the attachments are subjectively shaped appropriately. Currently, it is not possible to verify the contact between the tooth and the attachment, or the contact between the attachment and the aligner. The OCT based methods and apparatuses described herein not only allow monitoring of these contacts, but may also permit high-resolution (e.g., on the order of about 5 µm) imaging, sufficient to detect slight deviations in attachment shape, positioning, and/or contact.

The methods and apparatuses (e.g., systems) described herein may also allow for the high accuracy dimensional analysis of attachments, including determining the geometric shape as well as the relative position on the tooth of each aligner. These methods and apparatuses may also be used to determine if attachment placement is compatible with planned orthodontic treatment, and may identify required adjustments to attachments (if needed). This may dramatically decrease the chair time the doctors need to spend with each patient and could also increase treatment efficacy by reducing poor attachment placements. These apparatuses may also allow the treating doctor to approve the attachments remotely (e.g., from his/her office or off site).

For example, a method of placing attachments on a tooth may include scanning and examination (manual or automatic) of the connection between the teeth and the attachment. As mentioned, an attachment may be a from that is configured to mount to a tooth and extend from the outer surface of the tooth, such as the buccal and/or lingual surface. The attachment may be formed of a polymeric material, a metallic material or some combination thereof. For example, the attachment may be a small, tooth-colored projection formed of dental bonding material (e.g., white filling material) that is placed at a specific locations on a specific tooth, e.g., at about the middle of the tooth, such as at a level that's halfway between the biting edge and gum line of the tooth. An attachment may be any appropriate shape, e.g., rectangular, square, circular, ellipsoidal, crescent, triangular, etc. The shape and orientation of an attachment (which may also be referred to herein as a 'power ridge') may be related to the purpose it serves (e.g., tooth rotation, translation, intrusion or extrusion). For example, an ellipsoidal (e.g., oval) attachment may measure about $\frac{1}{16}$th of an inch wide, a little more than that in height, and roughly $\frac{1}{32}$nd inches thick. In some variations the attachment may be referred to as a power ridge that is configured to adjust the force applied by the aligner on the tooth or teeth; thus an attachment may, but is not limited to, attachments that connect secure or connect the aligner to the teeth. For example, an attachment (configured as a power ridge) may be formed of a dental filling material that is placed in strategic location on a tooth, e.g., at the gum line on the front side of a tooth that's inclined backward (e.g., tipped inward). A second ridge may be placed on the same tooth but on its backside up near the tooth's biting edge, so that applying pressure simultaneously at these two high and low points on opposite sides of the same tooth from the aligner may help tip or rotate the tooth forward, presumably into a more normal alignment (reversing the positioning of the power ridges may be used to produce a tilting in/backward rotation, for example).

Thus, the methods described herein may aid in placing and confirming the bonding between the attachment and the tooth. In one example, the method (or an automated apparatus configured to perform the method) may include receiving or taking a model of the patient's existing tooth and/or all or a portion of the dentition (upper arch and/or lower arch). For example, the method may include modeling a patient's existing dental configuration by forming a digital model (scanning, e.g., with an intraoral scanner) the patient's dentition or a dental impression taken from the patient. This initial model may be a digital model. In some variations, this digital model of the patient's teeth may be imported from the treatment plan and used for registration purposes.

One or more attachments may be placed on the patient's tooth/teeth. The attachments may be applied to the teeth using any appropriate protocol. One or more guides (e.g., jigs) may be used.

Once the attachments are placed on the teeth (all or some of them), the teeth and attachments may be jointly scanned, preferably using a high-resolution (e.g., having a resolution of better than 10 µm). For example, an optical scan of the surface of the tooth/teeth (e.g., the buccal and/or lingual surfaces of the teeth) may be taken, either in segments or the entire arch. If taken in segments, the segments may be stitched together. In some variations, the scanner may visualize the attachment composite; preferably the scanner may also take a penetrative scan, e.g., using optical coherence tomography (OCT) to visualize through the composite forming the attachment. This may allow the scanner to visualize defects in the material (e.g., composite) forming that attachment, such as cracks and/or voids and to differentiate attachment material from enamel.

Thereafter, the geometry and relative placement of the attachment(s) relative to the tooth/teeth including for all teeth) may be determined. For example, the geometry may be calculated as described above, and/or by subtraction from the pre-scan of the teeth taken prior to connecting the attachments to the teeth. In some variations the attachments may be isolated directly segmenting them from off from the OCT image.

The attachments may be analyzed, e.g., by shape analysis of the attachments, and compared with the intended attachment locations and/or shapes based on the treatment plan or on a database of expected attachment shapes. This analysis may be automated. For example an analysis engine of an apparatus (which may be software, firmware and/or hardware) may comprise an automated agent configured to analyze the attachment(s) and confirm that they are of the proper size and shape and/or are free from defects such as cracks, voids, inclusions, etc. the analysis engine may also confirm the location and/or orientation of the attachment; this confirmation may be based on a comparison with a treatment plan specific to the patient, to confirm that the one or more attachments are within an acceptable tolerance of the clinical treatment plan. In general a clinical treatment plan may include a timeline of patient treatment detailing movement of the patient's teeth and/or the configuration of the aligner(s), attachments and any additional components in order to reposition the patient's teeth into each of a series of desired positions during the treatment.

Any of the methods and apparatuses may also be configured to provide an output to an operator (e.g., user) indicating the status of the attachments. For example, the output may include one or more visual cues that may be presented to the operator showing that the attachment setup is acceptable or indicating specific adjustments that may be done with the attachment. In one example, the output includes displaying on a display an image of the patient's tooth/teeth including the attachment(s) and a color, pattern, or other indicator along with guiding instructions such as "remove flash here", "fill in void", "attachment placement is off, take it off and replace it". For example, the image may show in color regions that must be removed/trimmed, etc. In some variations the attachment(s) may be colored with one or more colors and/or intensities to indicate the level of tolerance with the expected shape/size/location/orientation of the attachment(s).

Once adjustment has been made, the teeth and attachment(s) may be rescanned and the process repeated, until acceptable adjustments have been made. When attachments are placed and/or adjusted by a dental technician, the dental professional (e.g., a supervisor, doctor, orthodontist, etc.) may be notified. The method and apparatus may further output overlays showing a direct side-by-side or one-on-top-of-the-other comparison of actual vs. ideal arrangement of the attachments on the tooth/teeth. For example a visuals of the real vs. planned attachment geometries can be overlaid and compared. The dental professional may then either approve the attachment(s) or indicate additional changes. This indication may be made through a computer interface (e.g., when operating remotely).

Alternatively in some variations, the methods and apparatuses may review and/or confirm the contact region(s) of the one or more attachments and the aligner. For example, OCT may be used to scan the aligner on the teeth and contacts, as described above. Regions of contact between either or both the aligner and/or the teeth may be identified.

In some variations, regions of contact (e.g., overlap) between the aligner and the attachments and/or aligner and teeth may be output to the user (e.g., dental professional, technician, etc.) as a graphical output, as mentioned above. For example, regions of contact between the aligner and the teeth may be highlighted by a color or pseudo-colored region in an image of the aligner and/or teeth, e.g., the aligner may be made transparent on the image, showing just the tooth/teeth and regions of contact. These regions may be highlighted and/or arrows (e.g., vectors) may be indicated in a predicted direction of the force, based on the expected or known tooth and/or aligner geometry. This may aid the dental practitioner in reviewing the treatment and/or modifying the treatment plan. For example, if a region of contact shows or suggests tooth movement (rotation and/or translation) in an undesirable location, the dental practitioner may modify the current or future treatment plan to adjust and/or remove the predicted tooth movement. In some variations, the tooth movement may be modified by changing and/or adding attachments, etc.

In addition to regions of contact between the aligner and the teeth and/or attachments, any of these methods and apparatuses may also identify regions of gaps (separation) between the teeth and the aligner and/or between the attachments and the aligner. Gaps or spaces between the aligner and the teeth/attachments are, in many respects, as important and regions of contact, particularly when predicting the forces acting on the teeth and/or comparing to a desired tooth movement. This is because the force system established by the aligner and the teeth may include regions where the force on the teeth is negligible (e.g., near zero), and may provide regions and/or direction for tooth movement. Thus, the OCT imaging data that may be acquired as described herein may be generally used to analyze the force system including the aligner, attachments and teeth, and may aid in predicting tooth movement.

For example, OCT imaging data showing contact between an aligner and/or the patient's teeth may provide input to calculate a force system. In some variations the method or an apparatus performing it may model forces acting on the teeth based on the regions of contact identified by the OCT images. Finite element analysis (FEA) may be used to model (e.g., by matching to the patterns of contact and tooth positions) the forces acting on the teeth. Alternatively or additionally, defection of the aligner shape (as described above) may be used to estimate force acting on the teeth and therefore expected or predicted movement profiles for the teeth. These movement profiles (based at least in part on the force system analysis) may be used to predict tooth movement and timing and may be compared to the treatment plan to determine if the expected tooth movements and timing is within a reasonable tolerance of that described in the treatment plan.

In some variations, the scanning methods and apparatuses (e.g. OCT scanning) may be used to detect and/or monitor acute movement of the teeth before and immediately or shortly after applying the aligner. For example, in some cases, applying the aligner may result in instantaneous or near-instantaneous (e.g., within a few seconds, a minute, a few minutes, etc.) movement of some of the patient's teeth based on the forces applied by the applicator. For example, in some variations, forces applied by the applicator may move the teeth between 0.05-0.5 mm (e.g., relative to the soft tissue and/or the other teeth in the dental arch(es)) and may identified using the high-resolution OCT scanning described herein. In some variations, the teeth may be pre-scanned using the OCT-based scanning and then scanned immediately (within a few seconds or minutes) after first applying the aligner; small changes in tooth position between the initial (pre-scan) and subsequent (immediate post-scan) images may be identified. These changes may be used to predict tooth larger and/or longer term tooth movements, and may in some variations be used to model root position and/or orientation. This information may be refined by subsequent scanning, e.g., when additional subsequent aligners are applied to the patient's teeth, by taking pre-scan (before applying the second or subsequent aligner) and an immediate post-scan to identify immediate movements. For example, this information may be used to identify resistance centers of one or more teeth, which may allow more accurate modeling of the tooth, including roots, and prediction of its ability to move.

Although many of the variations described above illustrate the use of the methods and apparatuses to monitor the contact between an aligner and a patient's teeth, any of these method and apparatuses may also be used to verify production of the aligner. For example, these methods and apparatuses may be used to verify the quality of an aligner (e.g., examining it for cracks, voids, and/or other flaws) or the like while or after it is being manufactured, prior to providing it to a patient. For example, any of these methods may include examining an aligner on a model or form used to create (e.g., by thermoforming) the aligner. The model or form may be similar to, but distinct from, a target tooth position, as the model or form may overcorrect tooth position, e.g., by positioning the teeth beyond where the intended final position is in order to drive tooth movement, and/or may alter the shape and/or size of the patient's actual teeth in order to include clearance to allow for tooth movement. Thus, when scanning as described herein with a putative aligner on a manufacturing form or jig, the contact between the form/jig and the aligner may be uniform or semi-uniform, particularly over the regions corresponding to the ends (e.g., the occlusal surface regions) of the teeth.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Figures 20A, 20B:
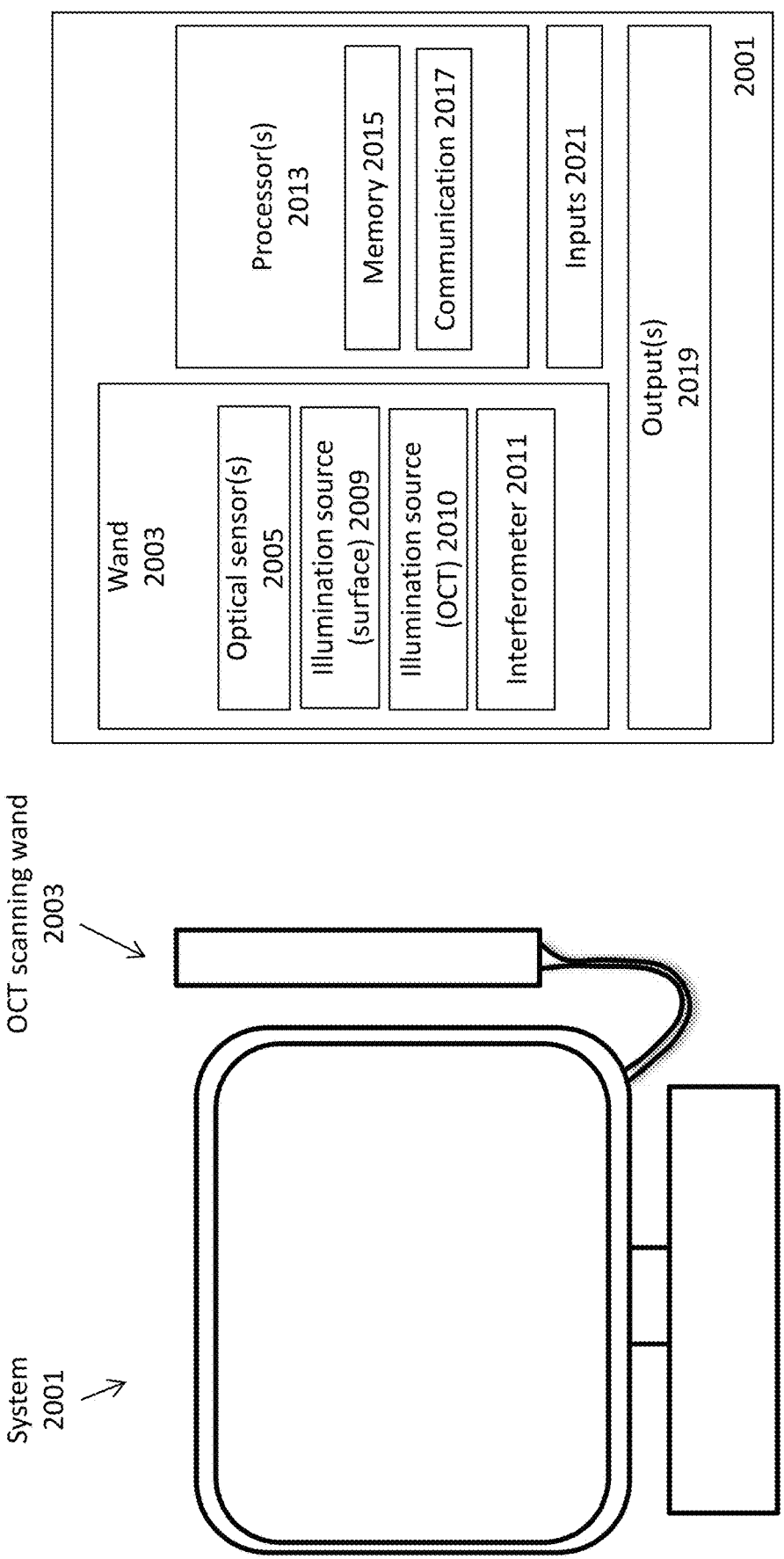
FIGS. 20A and 20B schematically illustrate examples of OCT systems as described herein.

For example, described herein are systems for processing a dental aligner and/or attachments using OCT imaging. FIGS. 20A and 20B schematically illustrate one example of a system. Any of these systems 2001 may include an OCT scanner 2003, one or more processors 2013 and a memory 2015 (or memories) that are coupled to the one or more processors, the memory configured to store computer-program instructions; these instructions may perform any of the methods described herein. Optionally, these systems may include a display/monitor (e.g., output 2019), one or more user inputs 2021 (e.g., keyboards, mice, buttons, dials, etc.). The OCT scanner may include a wand or hand-held scanning head for intraoral application 2003', and may be functionally connected or may include an OCT optical sensor 2005, an optional surface scanning sensor, a OCT illumination source 2010 (and an optional surface scanning source 2009), and the OCT circuitry, which may include an interferometer 2011, optics, optical cabling (e.g., fiber optics), etc.

Figure 21:
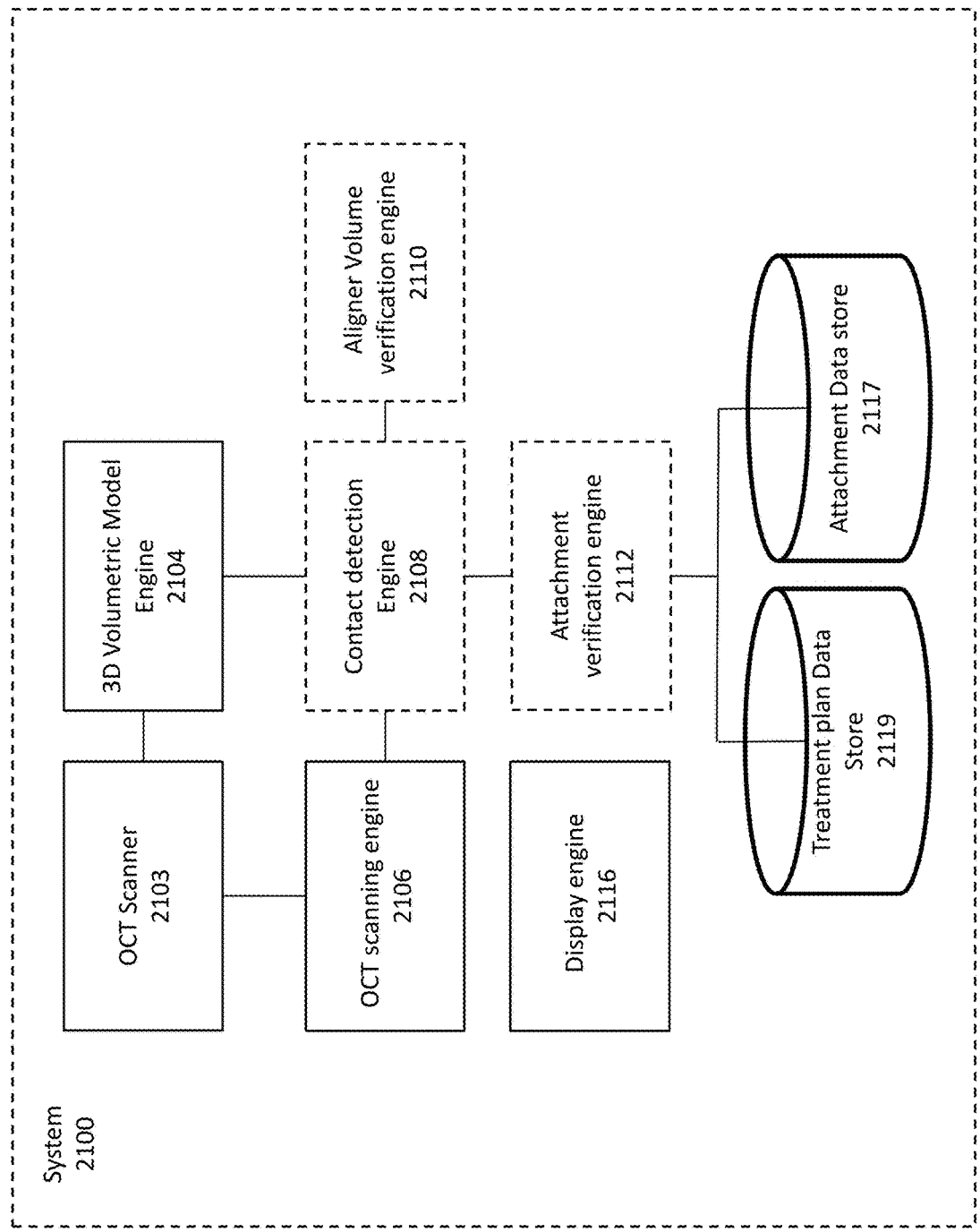
FIG. 21 is another example of a schematic of an OCT system.

For example, FIG. 21 illustrates another example of system (e.g., a computer system) for processing a dental aligner. In this example, the system 2100 includes an optical coherence tomography (OCT) scanner 2103, and one or more processors including a memory that is coupled to the one or more processors. The memory may be configured to store computer-program instructions, that, when executed by the one or more processors, perform a computer-implemented method. Any of these systems may include (as software or firmware, including as software executable by the one or more processors) a 3D volumetric engine that is capable of assembling a 3D volumetric model from scans (e.g., OCT scans) and/or visible light scans. For example, the 3D volumetric model engine 2104 may be configured to construct a 3D volumetric model of the patient's teeth (including any attachments on the teeth) and/or an aligner.

The system may also include an OCT scanning engine 2106 that scans, using the OCT scanner. The OCT scanning engine may be configured for operating on the patient's teeth and/or aligner(s). For example, the OCT scanning engine may be configured to scan a patient's teeth while a dental aligner is worn on the teeth (e.g., scanning both the dental aligner and the patient's teeth together). The system may also or optionally include a contact detection engine that may be configured to analyze one or more 3D models of the patient's teeth or teeth and aligners to determine contact between the aligner and the teeth and/or the aligner and an attachment on the teeth. The system may also or optionally include an aligner volume verification engine 2110 configured to analyze the volume of the aligner (e.g., automatically identifying cracks, voids, flaws, thin regions in the aligner. In some variations, the system may also or optionally include an attachment verification engine 2112 that analyzes (and may automatically identify) attachments on the patient's teeth, including looking for flaws in the attachment, miss-attachment, etc. An attachment datastore 2117 may include a variety of attachment configurations for comparison. Similarly a treatment plan datastore 2119 may store and aid in analysis of the aligner, attachments, tooth position, etc. Any of these systems may also include a display engine 2116 for displaying the one or more regions of contact.

In general, a computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, data stores are intended to include repositories having any applicable organization of data, including tables, comma-separated values (CSV) files, traditional databases (e.g., SQL), or other applicable known or convenient organizational formats. Data stores can be implemented, for example, as software embodied in a physical computer-readable medium on a specific-purpose machine, in firmware, in hardware, in a combination thereof, or in an applicable known or convenient device or system. Data store-associated components, such as database interfaces, can be considered part of a data store, part of some other system component, or a combination thereof, though the physical location and other characteristics of data store-associated components is not critical for an understanding of the techniques described herein.

Data stores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The data stores, described herein, can be cloud-based data stores. A cloud-based data store is a data store that is compatible with cloud-based computing systems and engines.

In general, any of the systems described herein may include any computer-readable medium configured to execute the steps of the methods described. Any of these systems may also or alternatively include without limitation a bus, a wired network, a wireless network, or some combination thereof.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of processing a dental aligner, the method comprising:
   scanning, using an optical coherence tomography (OCT) scanner, a patient's teeth while a dental aligner is worn on the teeth, wherein scanning comprises scanning both the dental aligner and the patient's teeth together;
   generating a three-dimensional (3D) model of the combined dental aligner and patient's teeth;
   detecting one or more regions of contact between the aligner and the patient's teeth from the 3D model; and
   displaying, storing and/or transmitting the 3D model.

2. The method of claim 1, wherein scanning comprises scanning a plurality of 3D volumes each comprising a set of voxels corresponding to the aligner and teeth.

3. The method of claim 2, wherein generating the 3D model comprises stitching the plurality of 3D volumes.

4. The method of claim 3, wherein generating the 3D model comprises filtering the 3D volume to remove noise prior to stitching the plurality of 3D volumes.

5. The method of claim 2, further comprising binarization of greyscale 3D volume intensity by identification of local intensity maximums for each Z-section.

6. The method of claim 2, further comprising parsing the plurality of 3D volumes to isolate an aligner outer surface, an aligner inner surface and a tooth surface.

7. The method of claim 6, further comprising smoothing each of the aligner outer surface, the aligner inner surface and the tooth surface.

8. The method of claim 6, further comprising correcting an optical path length of the plurality of 3D volumes after isolating the aligner outer surface, the aligner inner surface and the tooth surface.

9. The method of claim 6, further comprising displaying, on the 3D model, the detected one or more regions of contact.

10. The method of claim 6, further comprising estimating forces acting on the patient's teeth by the aligner using the detected one or more regions of contact.

11. The method of claim 1, wherein scanning comprises scanning in a near-IR wavelength using the OCT scanner.

12. The method of claim 1, wherein displaying, storing and/or transmitting the 3D model comprises displaying the 3D model in real time.

13. The method of claim 1, further comprising detecting gaps between the aligner and the patient's teeth from the 3D model.

14. The method of claim 13, further comprising displaying, on the 3D model, the detected gaps.

15. A system for imaging a dental aligner, the system comprising:
an optical coherence tomography (OCT) scanner;
one or more processors;
memory coupled to the one or more processors, the memory configured to store computer-program instructions, that, when executed by the one or more processors, perform a computer-implemented method comprising:
scanning, using the OCT scanner, a patient's teeth while a dental aligner is worn on the teeth, wherein scanning comprises scanning both the dental aligner and the patient's teeth together;
generating a three-dimensional (3D) model of the combined dental aligner and patient's teeth;
identifying one or more regions of contact between the patient's teeth and the dental aligner from the 3D model of the combined dental aligner and teeth; and
displaying the one or more regions of contact.

16. A method of processing a dental aligner, the method comprising:
scanning, using an optical coherence tomography (OCT) scanner, a patient's teeth while a dental aligner is worn on the teeth, wherein scanning comprises scanning both the dental aligner and the patient's teeth together;
generating a three-dimensional (3D) model of the combined dental aligner and patient's teeth;
identifying regions of contact between the dental aligner and the patient's teeth; and
displaying the regions of contact.

17. The method of claim 16, wherein displaying comprises interactively displaying, comprising allowing the user to rotate and/or zoom into the view.

18. The method of claim 16, wherein displaying comprises displaying a 3D model of the patient's teeth with the regions of contact indicated thereon.

19. The method of claim 16, further comprising modifying an orthodontic treatment plan including the aligner based on the regions of contact.

20. The method of claim 16, wherein the patient's teeth comprise one or more attachments, and further wherein identifying regions of contact between the dental aligner and the patient's teeth comprises identifying regions of contact between the dental aligner and the one or more attachments.

21. The method of claim 16, wherein displaying comprises displaying in a user interface accessible to a dental practitioner.

22. A method of processing a dental aligner, the method comprising:
scanning, using penetrative scanning, a patient's teeth while a dental aligner is worn on the teeth, wherein scanning comprises scanning both the dental aligner and the patient's teeth together, wherein scanning comprises scanning a plurality of 3D volumes each comprising a set of voxels corresponding to one or more of the aligner and the patient's teeth;
generating a three-dimensional (3D) model of the combined dental aligner and patient's teeth; and
displaying, storing and/or transmitting the 3D model.

23. The method of claim 22, wherein the penetrative scanning comprises optical coherence tomography (OCT).

24. The method of claim 22, wherein the penetrative scanning comprises near-infrared light scanning.

* * * * *